(12) United States Patent
Viscomi et al.

(10) Patent No.: US 9,498,442 B2
(45) Date of Patent: *Nov. 22, 2016

(54) RIFAXIMIN POWDER, PROCESS FOR PREPARING THE SAME AN CONTROLLED RELEASE COMPOSITIONS CONTAINING SAID RIFAXIMIN USEFUL FOR OBTAINING A LONG-LASTING EFFECT

(71) Applicant: ALFA WASSERMANN S.P.A., Alanno (IT)

(72) Inventors: Giuseppe Claudio Viscomi, Bologna (IT); Paola Maffei, Bologna (IT); Vittoria Lauro, Bologna (IT); Maria Barbanti, Bologna (IT); Donatella Confortini, Bologna (IT); Dario Braga, Bologna (IT)

(73) Assignee: ALFA WASSERMANN S.P.A., Alanno (IT)

( * ) Notice: Subject to any disclaimer, the term of this patent is extended or adjusted under 35 U.S.C. 154(b) by 0 days.

This patent is subject to a terminal disclaimer.

(21) Appl. No.: 14/261,337

(22) Filed: Apr. 24, 2014

(65) Prior Publication Data
US 2014/0235662 A1    Aug. 21, 2014

Related U.S. Application Data

(63) Continuation of application No. 13/582,676, filed as application No. PCT/IB2011/050933 on Mar. 4, 2011, now Pat. No. 8,748,447.

(30) Foreign Application Priority Data

Mar. 5, 2010 (IT) .......................... MI2010A000370

(51) Int. Cl.
*A61K 9/16* (2006.01)
*A61K 9/14* (2006.01)
(Continued)

(52) U.S. Cl.
CPC .............. *A61K 9/1682* (2013.01); *A61K 9/14* (2013.01); *A61K 9/2013* (2013.01);
(Continued)

(58) Field of Classification Search
None
See application file for complete search history.

(56) References Cited

U.S. PATENT DOCUMENTS 5,356,625 A    10/1994 Ying
5,840,332 A    11/1998 Lerner et al.
(Continued)

FOREIGN PATENT DOCUMENTS

EP    0547294 A1    6/1993
EP    061608 A1    9/1994
(Continued)

OTHER PUBLICATIONS

Non-Final Rejection issued by the US Patent and Trademark Office on Sep. 19, 2005 in U.S. Appl. No. 10/728,090.
(Continued)

*Primary Examiner* — Robert A Wax
*Assistant Examiner* — Melissa Mercier
(74) *Attorney, Agent, or Firm* — Steinfl & Bruno, LLP

(57) ABSTRACT

The present invention describes rifaximin powder and to a process for preparing the same. The invention relates also to a pharmaceutical composition in solid form comprising said rifaximin, pharmaceutically acceptable excipients and optionally other ingredients. The compositions according to the invention are suitable for oral administration and are characterized by producing a controlled release of rifaximin, whereby a long-lasting effect is obtained in a patient.

7 Claims, 10 Drawing Sheets

Plasma concentration profile after multiple administration of a 200 mg rifaximin tablet prepared as Example 3 and Normix® in the V7 subject

(51) Int. Cl.
  *A61K 9/20*    (2006.01)
  *A61K 9/28*    (2006.01)
  *A61K 31/437*  (2006.01)
  *C07D 498/16*  (2006.01)
  *C07D 498/22*  (2006.01)

(52) U.S. Cl.
  CPC .......... *A61K 9/2054* (2013.01); *A61K 9/2059* (2013.01); *A61K 9/2866* (2013.01); *A61K 31/437* (2013.01); *C07D 498/16* (2013.01); *C07D 498/22* (2013.01)

(56) References Cited

U.S. PATENT DOCUMENTS

| | | | |
|---|---|---|---|
| 7,709,634 B2 | 5/2010 | Kothakonda et al. | |
| 7,906,542 B2 | 3/2011 | Viscomi et al. | |
| 7,915,275 B2 | 3/2011 | Viscomi et al. | |
| 7,923,553 B2 | 4/2011 | Viscomi et al. | |
| 8,067,429 B2 * | 11/2011 | Gushurst et al. | 514/279 |
| 8,158,644 B2 | 4/2012 | Viscomi et al. | |
| 8,158,781 B2 | 4/2012 | Viscomi et al. | |
| 8,173,801 B2 | 5/2012 | Viscomi et al. | |
| 8,193,196 B2 | 6/2012 | Viscomi et al. | |
| 8,217,054 B2 | 7/2012 | Maffei et al. | |
| 8,227,482 B1 | 7/2012 | Parent et al. | |
| 8,318,763 B2 | 11/2012 | Viscomi et al. | |
| 8,404,704 B2 | 3/2013 | Viscomi et al. | |
| 8,518,949 B2 | 8/2013 | Viscomi et al. | |
| 8,569,326 B2 | 10/2013 | Gushurst et al. | |
| 8,748,447 B2 * | 6/2014 | Viscomi | A61K 9/14 514/279 |
| 2003/0059471 A1 | 3/2003 | Compton et al. | |
| 2005/0196418 A1 | 9/2005 | Yu et al. | |
| 2005/0272754 A1 | 12/2005 | Viscomi et al. | |
| 2008/0262024 A1 | 10/2008 | Viscomi et al. | |
| 2009/0028940 A1 | 1/2009 | Jahagirdar et al. | |
| 2009/0082558 A1 | 3/2009 | Kothakonda et al. | |
| 2010/0174064 A1 | 7/2010 | Gushurst et al. | |
| 2010/0330129 A1 | 12/2010 | Viscomi et al. | |
| 2011/0086871 A1 | 4/2011 | Viscomi et al. | |
| 2011/0105550 A1 | 5/2011 | Gushurst et al. | |
| 2012/0035202 A1 | 2/2012 | Viscomi et al. | |
| 2012/0076857 A1 | 3/2012 | Gushurst et al. | |
| 2012/0202989 A1 | 8/2012 | Viscomi et al. | |
| 2012/0203000 A1 | 8/2012 | Viscomi et al. | |
| 2012/0207833 A1 | 8/2012 | Parent et al. | |
| 2012/0214989 A1 | 8/2012 | Viscomi et al. | |
| 2012/0264774 A1 | 10/2012 | Parent et al. | |
| 2013/0004576 A1 | 1/2013 | Viscomi et al. | |
| 2013/0028971 A1 | 1/2013 | Viscomi et al. | |
| 2013/0066079 A1 | 3/2013 | Gushurst et al. | |
| 2013/0072676 A1 | 3/2013 | Maffei et al. | |
| 2013/0281697 A1 | 10/2013 | Viscomi et al. | |
| 2013/0287692 A1 | 10/2013 | Viscomi et al. | |
| 2013/0289269 A1 | 10/2013 | Viscomi et al. | |
| 2013/0310410 A1 | 11/2013 | Viscomi et al. | |
| 2014/0011828 A1 | 1/2014 | Gushurst et al. | |
| 2015/0073007 A1 | 3/2015 | Viscomi et al. | |

FOREIGN PATENT DOCUMENTS

| | | |
|---|---|---|
| EP | 0935417 B1 | 8/1999 |
| EP | 1676847 B1 | 7/2006 |
| EP | 1676848 B1 | 7/2006 |
| EP | 1698630 A1 | 9/2006 |
| EP | 1698630 B1 | 9/2006 |
| EP | 1874273 B1 | 1/2008 |
| EP | 2011486 A1 | 1/2009 |
| EP | 2059232 A1 | 5/2009 |
| EP | 2208730 A1 | 7/2010 |
| EP | 2210893 A1 | 7/2010 |
| EP | 2420226 A1 | 2/2012 |
| EP | 2421869 B1 | 2/2012 |
| EP | 2542225 B1 | 1/2013 |
| IT | 1154655 B1 | 11/1981 |
| IT | 1349654 | 10/2003 |
| NZ | 531622 B | 3/2004 |
| WO | 9000553 A1 | 1/1990 |
| WO | 9200302 A1 | 1/1992 |
| WO | 0214323 A2 | 2/2002 |
| WO | 0236542 A1 | 5/2002 |
| WO | 0243732 A1 | 6/2002 |
| WO | 2006094662 A1 | 9/2006 |
| WO | 2008029208 A1 | 3/2008 |
| WO | 2009008005 A1 | 1/2009 |
| WO | 2009008006 A2 | 1/2009 |
| WO | 2010044093 A1 | 4/2010 |
| WO | 2010067072 A1 | 6/2010 |
| WO | 2010122436 A1 | 10/2010 |
| WO | 2011050397 A1 | 5/2011 |
| WO | 2011051971 A2 | 5/2011 |
| WO | 2011061516 A2 | 5/2011 |
| WO | 2011061519 A2 | 5/2011 |
| WO | 2011061748 A1 | 5/2011 |
| WO | 2011080691 A1 | 7/2011 |
| WO | 2011088688 A1 | 7/2011 |
| WO | 2011103120 A1 | 8/2011 |
| WO | 2011107970 A2 | 9/2011 |
| WO | 2011110930 A2 | 9/2011 |
| WO | 2011153444 A1 | 12/2011 |
| WO | 2011156897 A2 | 12/2011 |
| WO | 2012009387 A1 | 1/2012 |
| WO | 2012009388 A1 | 1/2012 |
| WO | 2012035283 A1 | 3/2012 |
| WO | 2012035544 A2 | 3/2012 |
| WO | 2012038898 A1 | 3/2012 |
| WO | 2012076832 A1 | 6/2012 |
| WO | 2012109605 A2 | 8/2012 |
| WO | 2012150561 A1 | 11/2012 |
| WO | 2012156951 A1 | 11/2012 |
| WO | 2013017928 A1 | 2/2013 |
| WO | 2013185211 A1 | 12/2013 |
| WO | 2014091432 A1 | 6/2014 |
| WO | 2015014984 A1 | 2/2015 |

OTHER PUBLICATIONS

Response to Non-Final Rejection submitted on Jan. 17, 2006 in U.S. Appl. No. 10/728,090.
Restriction Requirement issued by the US Patent and Trademark Office on Jul. 16, 2013 in U.S. Appl. No. 13/582,676.
Response to Restriction Requirement submitted on Oct. 10, 2013 in U.S. Appl. No. 13/582,676.
European Patent N. 1557421, Opposition Proceedings, "Notice of Opposition to the European Patent," Feb. 11, 2008.
European Patent N. 1557421, Opposition Proceedings, "Patentee Response to Notice of Opposition," Sep. 10, 2008.
European Patent N. 1557421, Opposition Proceedings, "Patentee Response to Summons to Attend Oral Proceeding," Apr. 22, 2009.
European Patent N. 1557421, Opposition Proceedings, "Opponent Response to Summons to Attend Oral Proceedings," Apr. 23, 2009.
European Patent N. 1557421, Opposition Proceedings, "Patentee Response to Brief Communication," May 29, 2009.
European Patent N. 1557421, Opposition Proceedings, "Opponent Response to the Late Submission of Patentee," Jun. 11, 2009.
European Patent N. 1557421, Opposition Proceedings, "European Patent Office Decision Rejecting the Opposition," Jul. 8,2009.
European Patent N. 1557421, Opposition Proceedings, Appellant Notice of Appeal , Sep. 18, 2009.
European Patent N. 1557421, Opposition Proceedings, Appellant Statement of Ground for Appeal, Nov. 18, 2009.
European Patent N. 1557421, Opposition Proceedings, "Patentee Response to Opponent Statement Out the Ground of the Appeal" Jun. 2, 2010.
European Patent No. 1557421, "Reply to the Communication pursuant to Article 96(2)," May 2, 2006.
European Search Opinion and European Search Report issued Jun. 6, 2006 for the European Patent Application No. 06004219.9.
Amendment filed before European Patent Office before Examination, Jul. 6, 2006 for the European Patent Application 06004219.9.

(56) References Cited

OTHER PUBLICATIONS

European Search Opinion and Search Report issued by the European Patent Office on Jun. 6, 2006 for European Application No. 06004220.7.
Amendment filed before European Patent Office before Examination on Jul. 6, 2006 for European Patent Application No. 06004220.7.
Report on Patentability issued on Apr. 16, 2012 by IPEA for the International Application No. PCT/IB2011/050933.
Response filed on May 7, 2012 to International Preliminary Examination Authorities for International Application No. PCT/IB2011/050933.
European Search Report issued by the European Patent Office on Jul. 14, 2004 for European Patent Application No. 04005541.0.
Official Communication issued by the European Patent Office on Feb. 16, 2006 for European Patent Application No. 04005541.0.
Reply to European Patent Office Official Communication submitted on May 3, 2006 for European Patent Application No. 04005541.0.
Official Communication issued by the European Patent Office on May 15, 2006 for the European Patent Application No. 04005541.0.
Reply to European Patent Office Official Communication submitted on Jun. 12, 2006 for European Patent Application No. 0405541.0.
Communication about Intention to Grant issued by the European Patent Office on Feb. 1, 2007 for European Patent Application No. 04005541.0.
Communication about Intention to Grant issued by the European Patent Office on Oct. 29, 2007 for European Patent Application No. 06004220.7.
Communication about Intention to Grant issued by the European Patent Office on Oct. 29, 2007 for European Patent Application No. 06004219.9.
Affidavit Viscomi submitted on Jan. 17, 2006 in U.S. Appl. No. 10/728,090.
European Patent N. 1557421, Opposition Proceedings, Summons to Attend Oral Proceedings, Jan. 19, 2009.
Dissolution Test for Solid Dosage Forms, European Pharmacopoeia Ed. 6.0, pp. 266-275, 2008.
Rifaximin, Merck Index XIIIed, p. 1475, Jan. 1, 2001.
Rifamycins, Merck Index XIII ed., p. 1474, Jan. 1, 2001.
Rifaximin, European Pharmacopoeia 6.5, pp. 4955-4957, Jan. 1, 2009.
Rifaximin, European Pharmacopoeia 7.1, pp. 3459-3460, Jan. 1, 2011.
Brufani M. et al., X-Ray Crystal Structure of 4-deoxy-3'-bromopyrido[1',2'-1,2]imidazo[5,4-c]Rifamycin S., J. Antibiot. (Tokyo), vol. 37 (12), pp. 1623-1627, Dec. 1, 1984.
Cellai L. et al., A study of structure-activity relationships in 4-deoxypyrido[1',2'-1,2]imidazo[5,4-c]rifamycin SV derivatives by electron spectroscopy for chemical analysis and 1H NMR, Mol. Pharmacol, vol. 27 (1), pp. 103-108, Jan. 1, 1985.
Cellai L. et al., Structure-activity relationships in 4-deoxypyrido[1',2'-1,2]imidazo[5,4-c]rifamycin SV derivatives., Farmaco, vol. 44 (2), pp. 97-107, Feb. 1, 1989.
Marchi E. et al., 4-Deoxypyrido[1',2':1,2]imidazo[5,4-c]rifamycin SV derivatives. A new series of semisynthetic rifamycins with high antibacterial activity and low . . . , J. Med. Chem., vol. 28 (7), pp. 960-963, Jul. 1, 1985.
Martinelli E. et al., Rifamycin R, a novel metabolite from a mutant of Nocardia mediterranea., J. Antibiot. (Tokyo), vol. 31 (10), pp. 949-951, Oct. 1, 1978.
Rao R.N. et al., On-line 2D-LC-ESI/MS/MS determination of rifaximin in rat serum., Biomed. Chromatogr., vol. 23 (11), pp. 1145-1150, Nov. 1, 2009.
Rossi C. et al., NMR Investigation of a New Semisynthetic Bioactive Compound, Bull. Magn. Reson., vol. 18 (1-2), pp. 87-90, Jan. 1, 1996
Sensi P. et al., Rifomycin, a New Antibiotic; Preliminary Report., Farmaco Sci., vol. 14 (2), pp. 146-147, Feb. 1, 1959.
Sensi P. , A Family of New Antibiotics, the Rifamycins. In: "Research Progress in Organic-Biological and Medicinal Chemistry"—Societá Editoriale Farmaceutica, Edited by U. Gallo, L. Santamaria. vol. 1, pp. 337-421. Jan. 1, 1964.
Venturini A.P., Pharmacokinetics of L/105, a New Rifamycin, in Rats and Dogs, After Oral Administration., Chemotherapy, vol. 29 (1), pp. 1-3, Jan. 1, 1983.
Stradi R. et al., Structural elucidation of the Rifaximin Ph. Eur. Impurity H., J. Pharm. Biomed. Anal., vol. 51 (4), pp. 858-865, Mar. 11, 2010.
ICH Topic Q 6 A, Specifications: Test Procedures and Acceptance Criteria for New Drug Substances and New Drug Products: Chemical Substances, European Medicines Agency, pp. 1-32. May 1, 2000.
Italian Product Label for NORMIX (Rifaximin), 6 pgs. Apr. 23, 1985.
Rifaximin—Intrinsic Dissolution—Experimental Data, 1 pg. Apr. 1, 2009.
Kibbe, A.H., Propylene Glycol. Handbook of Pharmaceutical Excipients., American Pharm. Association and Pharm. Press. vol. 165, pp. 442. Jan. 15, 2000.
NORMIX, Riassunto Delle Caratteristiche Del Prodotto, 15 pg. Jun. 1, 2000.
NORMIX, NORMIX 200 mg Compresse Rivestitte Con Film Normixfoglietto Illustrativo, 12 pg. 2012.
Cellai, L. et al., Rifaximin (L/105), a New Topical Intestinal Antibiotic: Pharmacokinetics Study After Single Oral Administration of 3H-Rifaximin to Rats, Chemioterapia, vol. III (6), pp. 373-377, Dec. 1, 1984.
Bacchi A. et al., Sampling rifamycin conformational variety by cruising through crystal forms: implications for polymorph screening and for biological models., 2008, 1725-1735, 32, New J. Chem.
Henwood S.Q. et al., Solubility and dissolution properties of generic rifampicin raw materials., 2000, 403-408, 26 (4), Drug Dev. Ind. Pharm.
Morris K.R. et al., Theoretical approaches to physical transformations of active pharmaceutical ingredients during manufacturing processes., 2001, 91-114, 48, Adv. Drug Deliv. Rev.
Morris K.R., Structural aspects of hydrates and solvates. In:"Polymorphism in pharmaceutical solids" edited by H.G. Brittain, 1999, 125-181, Drugs and the Pharmaceutical Sciences, vol. 95, Chap. 4.
Pelizza G. et al., Polymorphism of rifampicin., 1977, 471-481, 32 (7), Farmaco Sci.
Rodríguez-Spong B. et al., General principles of pharmaceutical solid polymorphism: a supramolecular perspective., 2004, 241-274, 56, Adv. Drug Deliv. Rev.
Vippagunta S.R. et al., Crystalline solids., 2001, 3-26, 48, Adv. Drug Deliv. Rev.
Qing Li et al., Solvothermal growth of vaterite in the presence of ethylene glycol, 1,2-propanediol and glycerin., 2002, 357-362, 236, J. Crystal Growth.
Andreas Hotter, Preparation of Raw Rifaximin and of Dried Raw Rifaximin According to Example 1 of EP 1698630—Andreas Hotter, May 29, 2015, 1-6.
Arthur Pichler, Analysis Via Powder X-Ray Diffraction of Current NORMIX Tablets—Arthur Pichler, May 29, 2015, 1-9.
Dana Hoffmann, Rifaximin, Oral Bioavailability Study in Dogs of Four Different Polymorphic Isoforms—Dana Hoffmann, Mar. 6, 2015, 1-4.
Mino R. Caira , Crystalline Polymorphism of Organic Compounds, 1998, 164-208.
Henck Jan-Olav, Polymorphie von Arzneistoffen Eine wirtschaftliche Herausforderung, 1997, 165-169, 59, Pharm Ind. Original German with English Translation.
Braga D et al., The Structure-Property Relationship of Four Crystal Forms of Rifaximin, 2012, 6404-6411, 14, CrystEngComm.
Cruz-Cabeza, Conformational polymorphism, 2013, 2170-2191, American Chemical Society.
Guillory, Generation of polymorphism, hydrates, solvates, and amorphous solids, 1999, 183-226.
Bauer et al., Ritonavir: an extraordinary example of conformational polymorphism, 2001, 18, 859-866, Pharmaceutical Research.
Brittain, Polymorphism and solvatomorphism 2009, 2011, 100(4) 1260-1279 Journal of Pharmaceutical Sciences.

(56) References Cited

OTHER PUBLICATIONS

Corti et al., Application of derivative resolution of UV spectra to the quality control of rifaximine and its possible impurities, 1992, 67(3) 76-79, Pharm. Acta Helv.

Rossi et al., NMR studies of a new class of rifaximin-derived molecules: rifaximin OR (Open ring), 1996, J. Chem. Research (S), 268-269.

Martini et al., Solution structure of rifaximin and its synthetic derivative rifaximin OR determined by experimental NMR and theoretical simulation methods., 2004, 12, 2163-2172, Bioorganic & Mideicinal Chemistry.

Swanepoel, Quality evaluation of generic drugs by dissolution test: changing the USP dissolution medium to distinguish between active and non-active mebendazole, 2003, 55, 345-349, European Journal of Pharmaceutics and Biopharmaceutics.

Liu et al., Structure elucidation of two unknown oxydic degradation impurities of rifaximin, 2011, 23(7). 3251-3256.

Agrawal et al., Solid-state characterization of rifampicin samples and its biopharmaceutic relevance., 2004, 22, 127-144, European Journal of Pharmaceutical Sciences.

Son et al., A new respirable form of rifampicin, 2011, 78, 366-376, European Journal of Pharmaceutics and Biopharmaceutics.

Blandizzi et al., Impact of crystal polymorphism on the systemic bioavailability of rifaximin, an antibiotic acting locally in the gastrointestinal tract, in healthy volunteers, 2015, 9, 1-11, Drug Design, Development and Therapy.

Saifee et al., Drug polymorphism: a review, 2009, 2(4) 291-306, International Journal of Health Research.

Kremer et al., Re-emergence of tuberculosis: strategies and treatment., 2002, 11(2), 153-157 Expert Opin. Investig. Drugs.

Marchese et al., In vitro activity of rifaximin, metronidazole and vancomycin against Clostridium difficile and the rate of selection of spontaneously resistant mutants against representative anaerobic and aerobic bacteria, including ammonia-producing species, 2000, 46, 253-266 Chemotherapy.

Ticinumlab, TicinumLab example 9, Synthesis of 4-deoxy-4'methyl-pyrido-[1',2':1,2]imidazo[5,4c] ryfamicin SV, 2010, 1-2.

Ticinumlab, TicinumLab example 7, Synthesis of 4-deoxy-4'methyl-pyrido-[1',2':1,2]imidazo[5,4-c] ryfamicin SV, 2010, 1-2.

Zach System, Synthesis of rifaximin obtained according to examples 7 and 9 reported in EP 0161534—Zach System, 2010, 1-16.

* cited by examiner

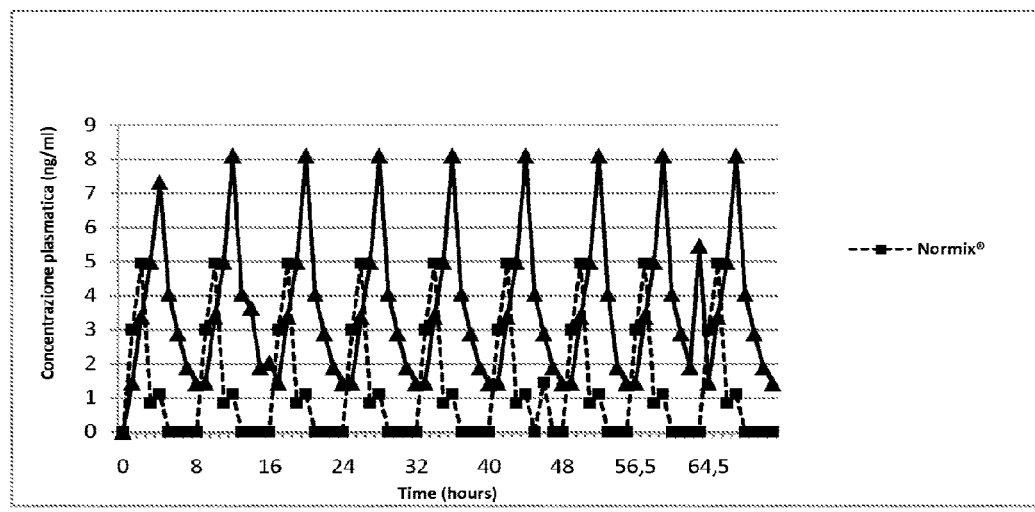
Figure 1: Plasma concentration profile after multiple administration of a 200 mg rifaximin tablet prepared as Example 3 and Normix® in the V7 subject

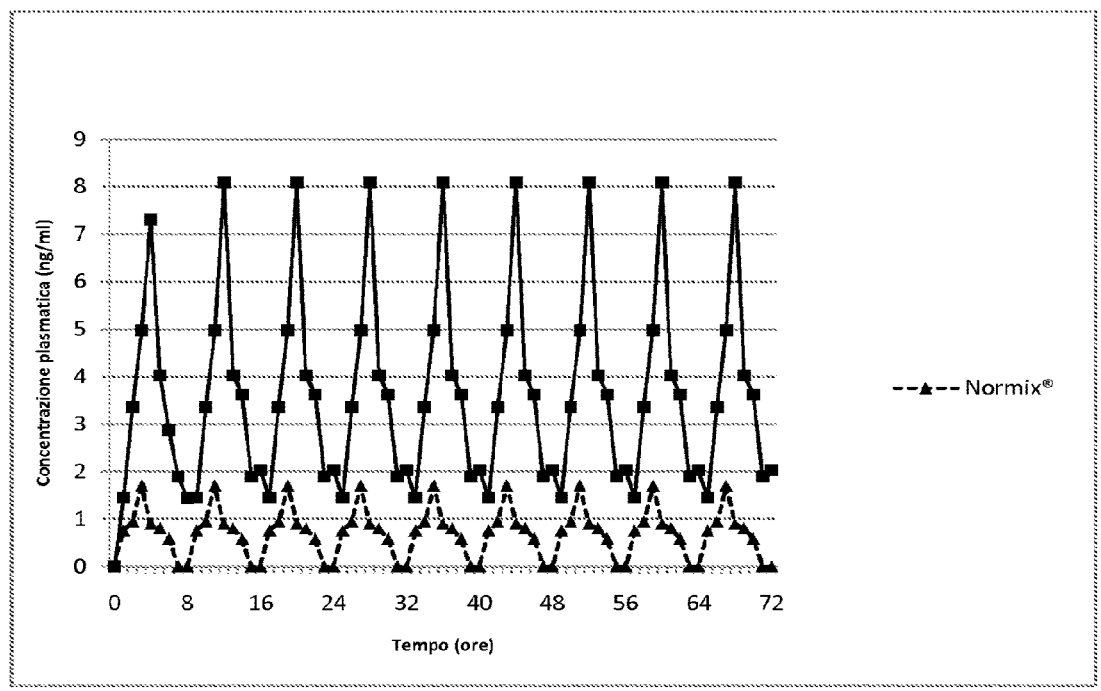
Figure 2 : Plasma concentration profile after multiple administration of a 200 mg rifaximin tablet prepared as Example 3 and Normix® in the V11 subject.

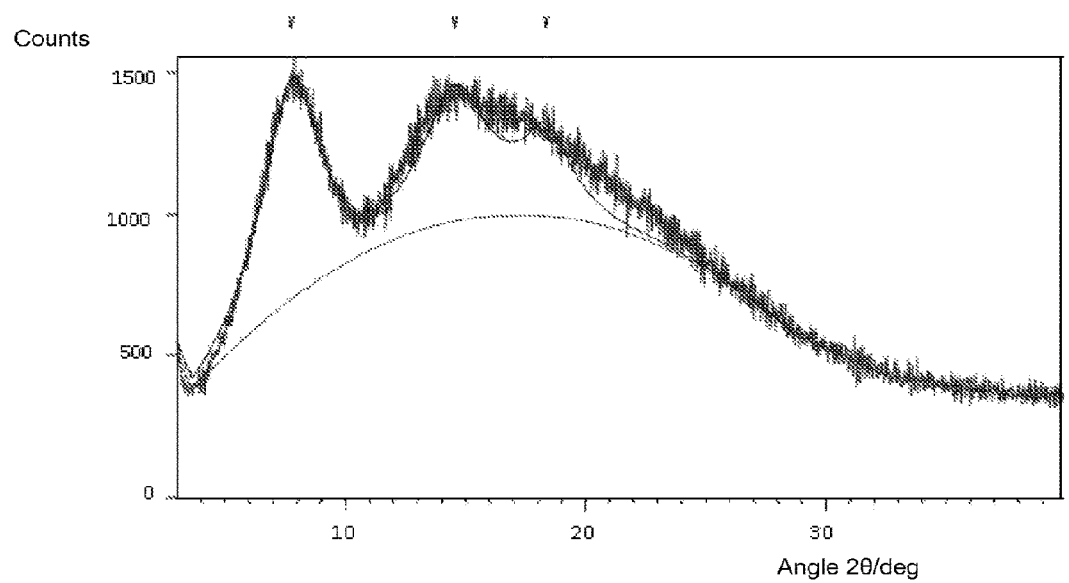
Figure 3: X-Ray diffraction spectra obtained by spray drying process.

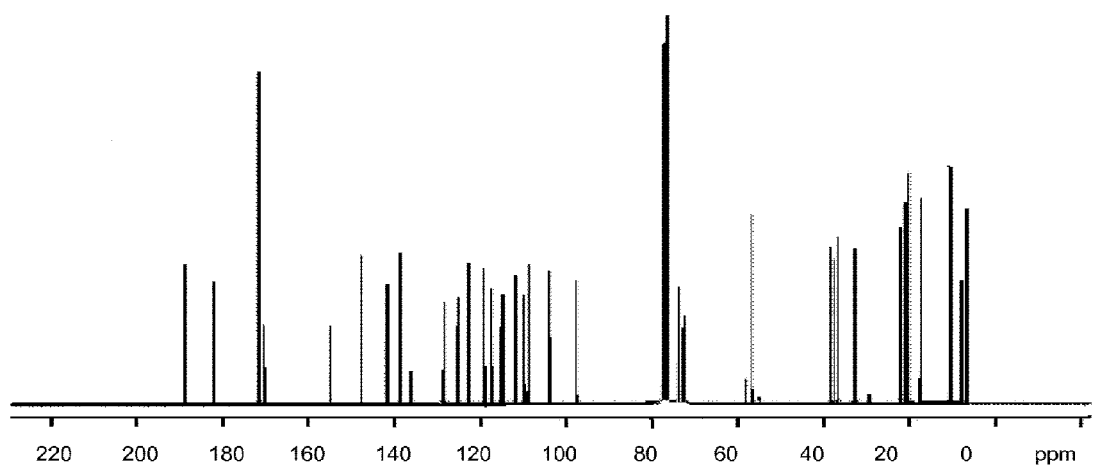
Figure 4: $^{13}C$ –NMR spectra obtained by spray drying process

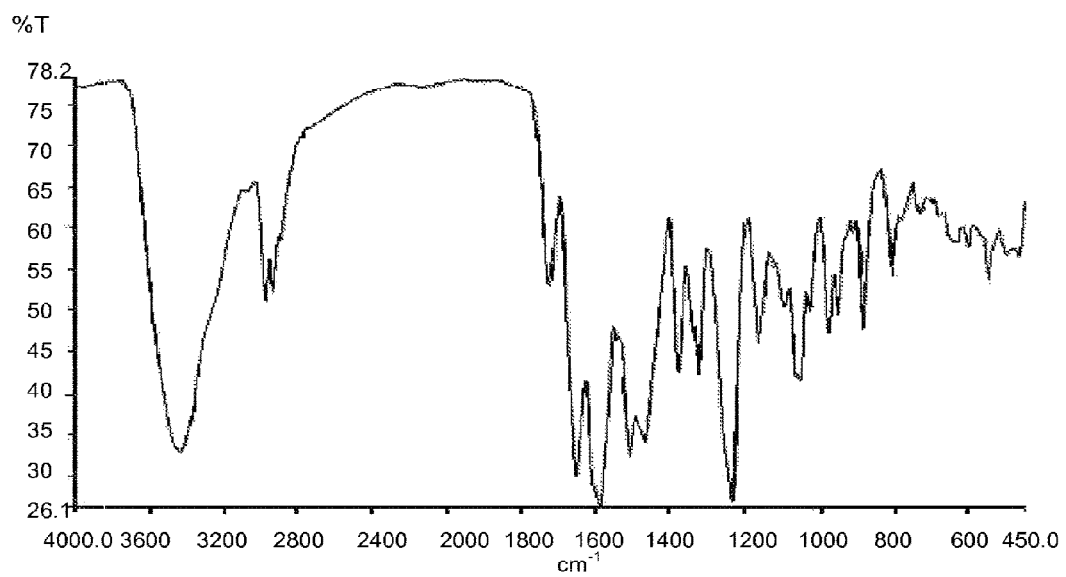
Figure 5: IR Spectra rifaximin obtained by spray drying process

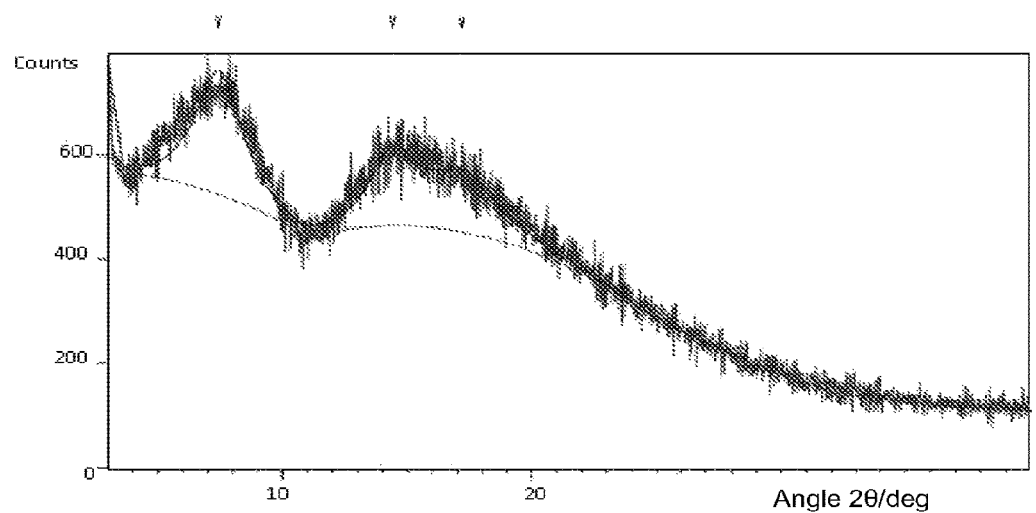
Figure 6 : X-Ray diffraction spectra of rifaximin obtained by milling process Figure 7: PSD rifaximin obtained by spray drying process

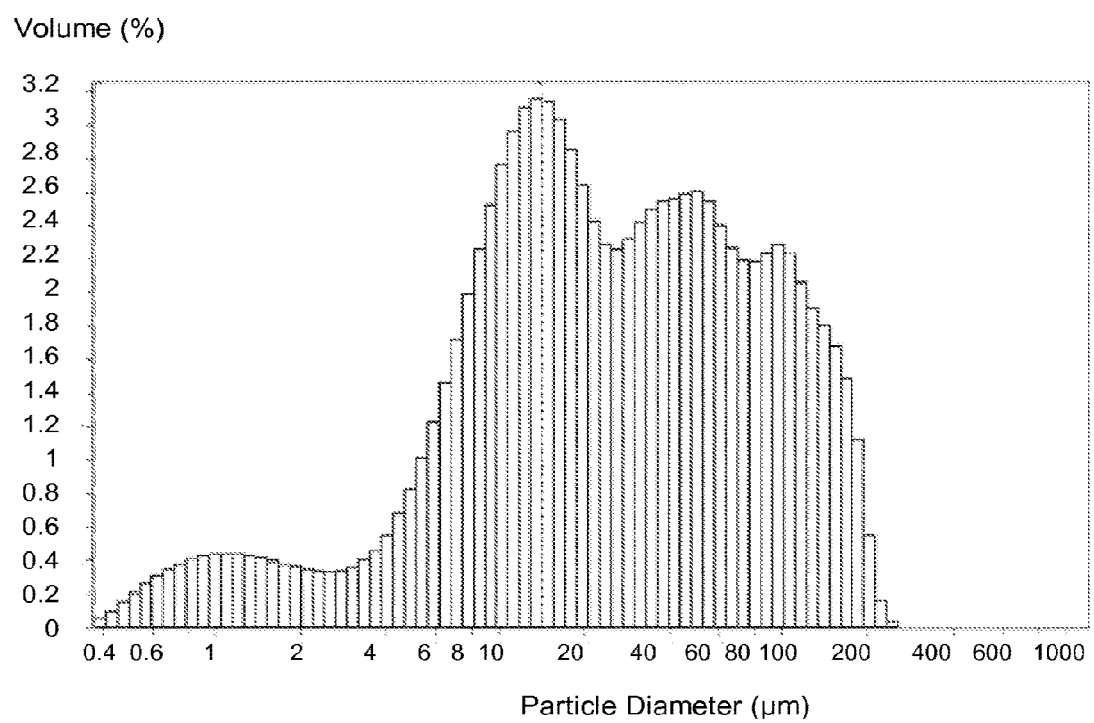
Figure 8 : PSD rifaximin obtained by milling process

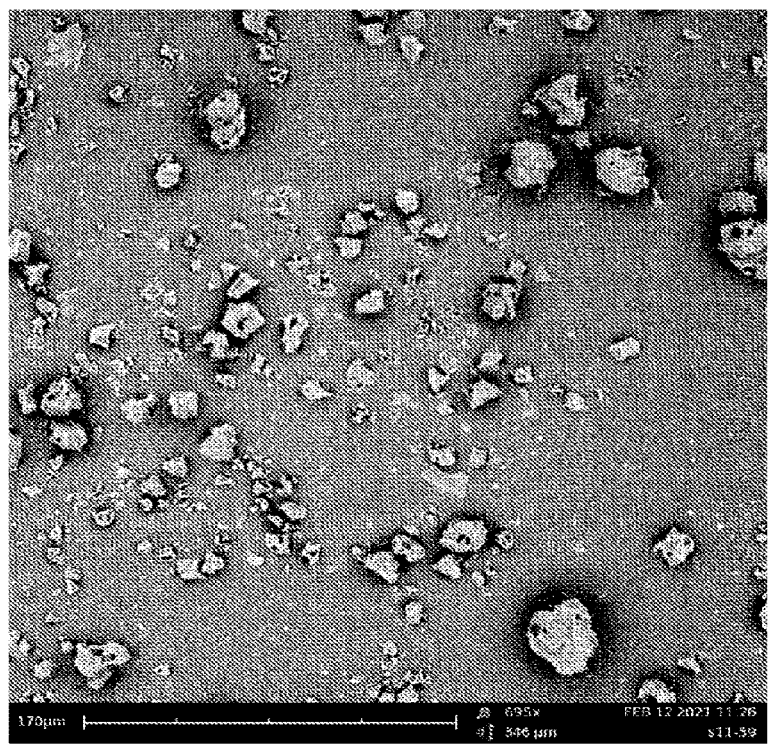
Figure 9: SEM Microscopy image of rifaximin obtained by spray drying process.

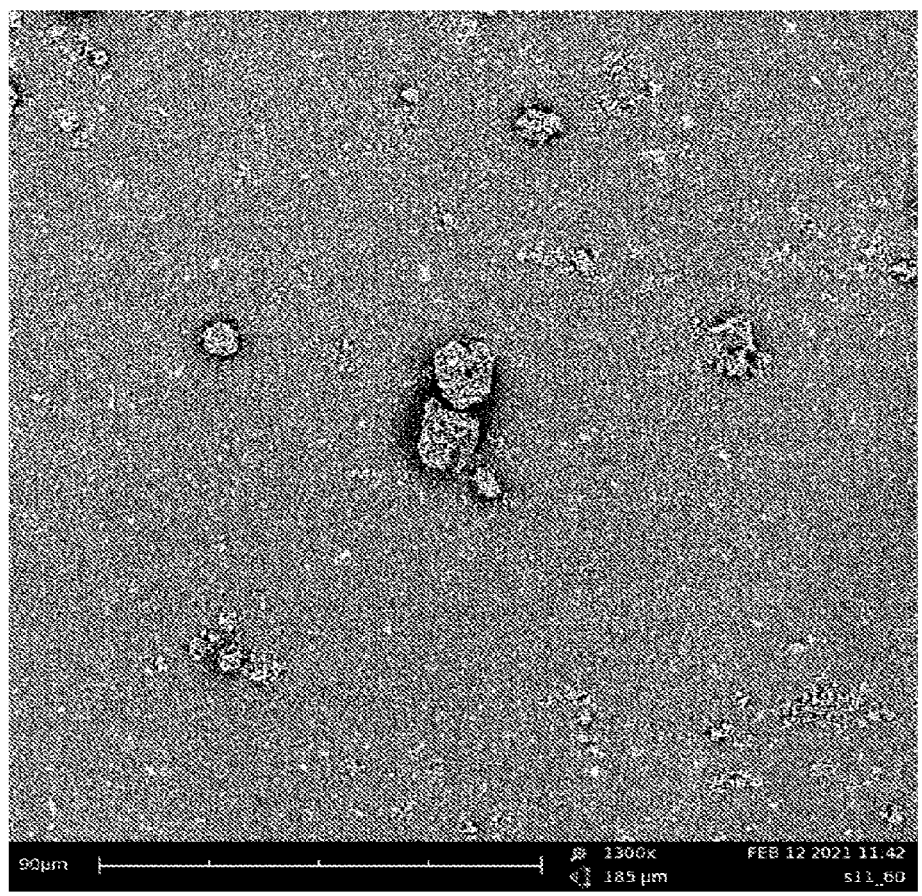
Figure 10: SEM Microscopy image of rifaximin obtained by milling process.

RIFAXIMIN POWDER, PROCESS FOR PREPARING THE SAME AN CONTROLLED RELEASE COMPOSITIONS CONTAINING SAID RIFAXIMIN USEFUL FOR OBTAINING A LONG-LASTING EFFECT

CROSS REFERENCE TO RELATED APPLICATIONS

This application is a US Continuation Application of Ser. No. 13/582,676 filed on Sep. 4, 2012 incorporated herein by reference in its entirety, which is the national phase of International Application PCT/IB2011/050933 filed on Mar. 4, 2011, which, in turn, claims priority to Italian Application MI2010A000370 filed on Mar. 5, 2010.

The present invention concerns rifaximin powder, a process for preparing the same, solid compositions comprising said rifaximin, and their use as a medicament.

STATE OF THE ART

Rifaximin (INN; see The Merck Index, XIII Ed., 8304, CAS no. 80621-81-4), IUPAC nomenclature (2S,16Z,18E,20S,21S,22R,23R,24R,25S,26S,27S,28E)-5,6,21,23,25 pentahydroxy-27-methoxy-2,4,11,16,20,22,24,26-octamethyl-2,7-(epoxypentadeca-(1,11,13)trienimino) benzofuro (4,5-e) pyrido(1,2,-a) benzimi-dazole-1,15(2H)-dione,25-acetate) is a semi-synthetic antibiotic belonging to the rifamycin class of antibiotics. More precisely rifaximin is a pyrido-imidazo rifamycin described in the Italian patent IT 1154655, whereas the European patent EP 0161534 discloses a process for rifaximin production using rifamycin O as starting material (The Merck Index, XIII Ed., 8301).

U.S. Pat. No. 7,045,620, US 2008/0262220, U.S. Pat. No. 7,612,199, US 2009/0130201 and Cryst. Eng. Comm., 2008, 10 1074-1081 (2008) disclose new forms of rifaximin.

WO 2008/035109 A1 discloses a process to prepare amorphous rifaximin, which comprises reaction of rifamycin S with 2-amino-4 picoline in presence of organic solvent like dichloromethane, ethylacetate, dichloroethylene, chloroform, in an inert atmosphere. When water is added to the reaction mixture, a solid precipitate corresponding to amorphous rifaximin is obtained.

The process described in this document can be assimilated to a crash precipitation, wherein the use of an anti-solvent causes the precipitation of rifaximin without giving any information about the chemical physical and biological characteristics of the rifaximin obtained.

WO 2009/108730 A2 describes different polymorphous forms of rifaximin and also amorphous forms of rifaximin. Amorphous forms are prepared by milling and crash precipitation and with these two different methods the amorphous rifaximin obtained from these two different processes has the same properties.

From prior art it appears that rifaximin, in amorphous form has always the same properties independently by the obtaining process.

Rifaximin, characterized by a systemic adsorption depending by the solid forms, in particular by the crystalline or amorphous forms, is known for its antibacterial activity exerted, for example, against bacteria localized in the gastrointestinal tract that cause, for instance, infectious bowel diseases, diarrhoea, irritable bowel syndrome (IBS), small intestinal bacterial overgrowth (SIBO), Crohn's disease (CD), pancreatic insufficiency, enteritis, fibromyalgia.

Antibiotics or combinations of antibiotics such as, for instance, neomycin, metronidazole, ciprofloxacin, doxycycline, tetracycline, penicillin, ampicillin, kanamycin, rifamycin, vancomycin and rifaximin are used in the therapy against bacterial bowel infections. Among them the antibiotics having a low systemic adsorption are preferred, such as, for instance, some crystalline forms of rifaximin. Antibiotics having a low systemic adsorption typically have an adsorption lower than 10%, and in particular between 0.05% and 1% of the nominal concentration.

The intestinal apparatus is subject to various inflammatory pathologies, generally termed as bowel diseases, known in the literature as "intestinal bowel disease" (IBD), and among them a particular relevance is given to IBS and CD.

IBS is a bowel disease affecting 10-20% of the adult population in Western countries. It is a disease characterized by a chronic recurrence of symptoms such as abdominal pain, swelling, meteorism, feelings of urgency or incomplete evacuation, and it is associated to alterations of the intestinal activity.

CD is a chronic inflammatory disease affecting various levels of the digestive tract, from the mouth to the anus. It is prevailingly localized in the last part of the small intestine, called ileum, thus taking the name of terminal ileitis, or in the colon, thus taking the name of colitis, or in both regions (thus taking the name of ileocolitis), but sometimes only in the colon mucosa and in the anal region. The affected intestinal tracts show inflammation, swelling and ulcerations in the whole intestinal wall, often causing stenosis and bleeding ulcers, whereas the tissue interposed between the sick areas appears normal. There is an alternation of periods with inflammatory manifestations of variable gravity and of periods of remission, wherein the main symptoms are represented by diarrhoea, abdominal pain and weight loss, often accompanied by rhagades or perirectal fistulas, frequently requiring a surgical treatment.

Although, generally speaking, the aetiology of inflammatory diseases is still in need of further investigations, some genetic, inflammatory, infective, nutritional, immune-mucosal and neuro-immune-mucosal factors have been found out. However, three theories have been most successful: the presence of a chronic infectious stimulus, a defect of the mucosal barrier and an altered response of the membrane immune system to autologous antigens.

The role of the intestinal bacterial flora in the aetiopathogenesis of intestinal inflammatory pathologies, and in particular in Crohn's disease, is remarked by a series of unmistakable signs: the disease is more frequently localized in areas with high bacterial concentrations, as described by Janowitz H. D. et al. in Inflamm. Bowel Dis. 1998, 4, 29-39; the diversion of the faecal flow leads to the remission of the endoscopic lesions which reappear again at restoration of the canalization, as described by Rutgeerts P. et al. in Lancet, 1991, 338, 771-774; in experimental models of knockout mouse for the IL-IO gene or others, the spontaneous colitis does not develop if the "germ-free" condition is maintained, as described by Blumberg R. S. et al. in Curr. Opin. Immunol., 1999, 11(6), 648-56; the inflammation of the intestinal mucous membrane develops as a consequence of the contact with the faecal material, as described by Harper P. H. et al. in Gut, 1985, 26(3), 279-84; in the case of patients submitted to a surgical "curative" therapy consisting of ileocolic anastomosis, the antibiotics treatment delays the development of both endoscopic and clinic relapses, as described by Cameron J. L. et al. in Ann. Surg., 1992, 215, 546-52; the presence of fistulas or abscess-sacs further points out the bacterial contribution to the disease development.

In medical therapy, medicaments able to reduce or control the inflammation such as cortisones, salazopirine, mesalazine, immunosupressants, specific chemotherapeutics, antibiotics and protein inhibitors of the actions of the Tumor Necrosis Factor (TNF) or of the adhesion of leucocytes, are largely used.

During the treatment of the acute phase of the inflammatory bowel disease, stronger treatments, such as parenteral alimentation, are often necessary to reconstitute the loss of proteins, liquids and salts, and above all to permit the intestine to rest in order to facilitate the cicatrisation of ulcers.

The purpose of the therapy is to decrease the frequency of the reappearance of symptoms and to reduce the seriousness of the acute episodes when they appear.

However, with current therapies, acute episodes respond in about 50-70% of the cases, but relapses occur in 80% of the patients.

Antibiotics are largely used to decrease the growth of the luminal bacteria and therefore to decrease the inflammatory state sustained as a result of the bacterial growth; to reduce symptoms of the acute phase of the disease, e.g., diarrhoea, intestinal pain and meteorism; and to prevent and to cure septic complications, such as abscesses, fistulas and toxic state.

The most frequently used antibiotics are systemically absorbed, for example, metronidazole, active against some parasites and many anaerobic bacteria, and ciprofloxacin, active against such bacteria as *E. Coli* and aerobic enterobacteriaceae.

Metronidrazole has been used at a dose of 10-20 mg/kg/day for 4 months, as described by Sunterland, L. Gut, 199132, 1071-5, while ciprofloxacin has been used at a dose of 1000 mg/day for 6 weeks, as described by Colombel J. F. in Am. J. Gastoenterol., 1999, 94, 674-8, while Prantera C. et al. in Am. J. Gastoenterol., 1996, 91, 328-32, adopted the combination of the two aforesaid antibiotics using metronidazole at the dose of 1000 mg/day and ciprofloxacin at the dose of 1000 mg/day for 12 weeks.

Unfortunately, the high systemic bioavailability of these antibiotics is at the basis of their high incidence of side effects registered in long-term therapies, which negatively impacts their use.

It is advantageous for a pharmaceutical preparation based on antibiotics used for efficaciously treating inflammatory bowel diseases to have one or more of the following characteristics: intestinal level activity, bacteria level control in the intestinal lumen, wide spectrum of actions against the microbes (e.g., intestinal Gram-positive, Gram-negative, aerobic and anaerobic components), possibility of long term therapy without severe side effects, ease of administration to facilitate compliance even with the potential of high dosage necessity.

An antibiotic possessing several of these characteristics is rifaximin, which is characterized by a wide spectrum of actions against many Gram-positive and Gram-negative bacteria, including aerobic and anaerobic bacteria. Bioavailability studies in healthy volunteers have shown that, when administered orally, less than 1% of rifaximin is absorbed and it concentrates in the intestinal lumen and in the faeces. This has been confirmed in patients affected by chronic bowel disease by Rizzello F. et al., Eur. J. Clin. Pharmacol. (1998) 54, 91-93.

The low systemic absorption of rifaximin reduces the incidence of side effects, adverse events and the unwanted risk of pharmacological interactions. Thus, rifaximin may be considered useful in the therapy of inflammatory chronic bowel disease.

Presently, rifaximin is approved for the treatment of pathologies whose aetiology is in part or totally due to intestinal acute and chronic infections sustained by Gram-positive and Gram-negative bacteria, with diarrhoea syndromes, altered intestinal microbial flora diarrhoea like summer diarrhoeic episodes, traveller's diarrhoea, enterocolitis, pre- and post-surgery prophylaxis of the infective complications in gastro intestinal surgery and as coadjutant in the hyperammonaemia therapy.

Rifaximin is currently marketed as tablets and capsules in ready-to-use preparations for a suspension, or as ointment for the treatment of topical infections, or as collyrium against ocular infections.

Xifaxan® tablets, commercialized in the US comprise polymorph a of rifaximin and its characteristics are reported in "Physicians' Desk Reference", 2007, vol. 62, pages 2790-2791, Thomson Healthcare, Montvale XP002601190, ISBN: 1-56363-660-3.

WO 2006/094737 A2 discloses gastroresistant compositions comprising rifaximin in polymorphs α, β, γ, δ and ε and it does not disclose the composition comprising amorphous rifaximin.

The preparation of coated microgranules is not easy with soluble power as amorphous rifaximin and WO 2006/094737 A2 does not give any information about process or composition to obtain coated particles in the presence of amorphous rifaximin.

The use of antibiotic in the clinical practice is directed by stringent control of dosage, both as amount of administered antibiotic and frequency of administration. Generally speaking, the target in antibiotic therapy is to provide plasma concentrations of antibiotics which never go below therapeutically significant thresholds over a time period of 3-7 days.

Usually these thresholds are established on the basis of the measure of the microbial inhibitory concentrations (MICS), which represent the lowest concentration of antibiotics to completely inhibit visible growth of microbial agents over a time period of about 18-24 hours at an incubation temperature of about 35° C. Sometimes reference is made to MIC50 and MIC90 values, which are defined as the lowest concentrations capable of inhibiting the growth of 50% and 90% of microbial isolates.

Regarding possible adverse events connected to the use of antibiotics, the problem of bacterial resistance to the antibiotic in use is well known. Also in the hospital setting, the use of antibiotics is often associated with an increase in the frequency of antibiotic resistance, whereas a reduced consumption of antibiotics may be followed by a reduction of resistance to specific drugs, as described by Guillemot D. et al., Current Opinion in Microbiology, 1999, 2:494-498.

The purpose of choosing the antibiotic dosage is that of maintaining their plasma concentration never below some threshold values in order to guarantee the eradication of pathogenic microorganisms. In fact, if the plasmatic antibiotic concentrations were lower than those able to inhibit the bacterial growth, or in case of periods of therapy in which the antibiotic is absent, the eradication of pathogens would not be guaranteed and, with an even more dramatic effect, the generation of bacteria resistant to antibiotics could be favoured. In the presence of concentrations lower than MICs, or when the antibiotic is not present, bacteria are in fact able to reproduce and to adapt, thus making the antibiotic action ineffective.

In the case of rifaximin it must be remarked that it is a locally-acting agent, which acts against pathogens which are present in the gastro-intestinal tract, on the mucosa surface or on the intestinal mucosa.

One of the mechanisms of action of rifaximin is the alteration of virulence factor of the enteric bacteria pathogens. This mechanism occurs at supra-, but most importantly, also at sub-inhibitory concentrations of rifaximin such 32-folds lower than the MIC values. It is concluded by Debbia et al., J. Chemother. 20 (2), 186-94, 2008 that this lethal effect mainly depends on the time in which the antibiotic is in contact with the bacteria and does not appear to be influenced by the antibiotic concentration.

The relevance of rifaximin contact with bacteria in the mechanism of action is also supported by Jiang Z. D. et al. in Int. J. Antimicrob. Agents 35(3), 278-81, 2010, who shows that rifaximin is effective in the alteration of the virulence of enterotoxogenic *Escherichia coli* isolates even at a concentration 8-fold lower than MIC, at the condition of providing the continuous contact of rifaximin with the pathogens at such concentration for at least 24 hours. On the contrary, if the contact is maintained only for 8 hours, the virulence of the pathogens is not abolished.

The evidence reported by Jiang Z. D. stresses the importance of providing a continuous presence of rifaximin in both the small and large bowel during therapies treating pathologies wherein bacterial agents in the intestinal tract are the cause of the disease.

Combining the importance of the contact time of rifaximin with pathogens to be effective with the fact that these pathogens are localised in the bowel, it can be inferred that drugs which can provide a more lasting residence time of rifaximin in the bowel could result to be more effective.

In this respect it is therefore important to determine the rifaximin time of contact with pathogenic bacteria in the intestinal tract.

However, this information is hardly obtainable. In fact, as rifaximin is negligibly soluble in water, any in-vitro models do not accurately reproduce the complex intestinal environment. On the contrary, in-vivo studies on humans should foresee the use of a product marked with a radioactive isotope with the relative problems of formulation implied by the use of radioactive materials.

However, useful information on rifaximin bowel residence time can be indirectly obtained by speculating on the pharmacokinetic (PK) profile of rifaximin in humans, in which the concentration of the active ingredient or active moiety in biological fluid (blood, plasma, serum and/or urine) is measured as a function of time. Generally speaking, it can be stated that the PK profile of an orally administered compound has to be considered dependent by the transient amount of the compound in the small intestine, which is the main absorptive site. An increase in the amount of the compound in the small intestine or a prolonged residence time are both factors favouring the systemic absorption.

The contemporaneous presence of a compound in blood and in the small intestine does not necessarily occur, since a compound requires a certain period of time for passing from the intestine to the blood; period of time depending both from the characteristics of the compound and from the physiologic or pathologic characteristics of the subject. In a healthy subject, this period of time is usually approximately one hour.

The correlation between the systemic concentrations of a compound and the availability of the same in the small intestine is well known and largely exploited by pharmaceutical technology. In fact, in order to favour the absorption, measures are taken for increasing the presence of the compound in the small intestine. On the contrary, in order to oppose the systemic concentration, measures are taken for hindering the release of the compound in the small intestine, for instance employing colonic release technologies.

In conclusion, the systemic bioavailability of an orally administered compound also depends on all those characteristics of a drug which can affect the release and the duration of the permanence of the active ingredient in the intestine, such as the characteristics of the active ingredient, the drug composition comprising the active ingredient, and the form of the administered drug (e.g. tablets, capsules, suspensions, gastro-resistant preparations or controlled-release preparations).

Also, the drug preparation process has a particular relevance. In fact, through the preparation method both the dissolution profile and the disaggregation profile of the drug can be modulated, thus making the active ingredient more or less available.

These concepts are entirely applicable to rifaximin. Therefore, a rifaximin concentration detectable in the plasma at a certain time must correspond to a rifaximin amount present in the small intestine at an earlier time. The correlation between the rifaximin amount in the intestine and the following plasma concentrations depends on the absorption of rifaximin and on the time of passage into the small intestine.

Therefore, it can be stated that a maximum plasma concentration of rifaximin, measured at a certain time, corresponds to a maximum amount of rifaximin present in the small intestine. Obviously, the absence of rifaximin in the plasma at a certain time should be an indication that there was a period of time in which rifaximin was not present in the small intestine.

PK data of rifaximin after oral administration of 400 mg tablets in humans are reported by Descombe J. J. et al. in Int. J. Clin. Pharmacol. Res., 14 (2), 51-56, (1994). In particular, this document reports in Table II, that in most cases, sixteen out of eighteen subjects, no amount of rifaximin is detectable in the blood 4 hours after the administration, and in all cases there is no detectable amount 8 hours after the administration.

Since the product commercialized in the USA with the trademark XIFAXAN® containing rifaximin foresees the administration of a 200 mg tablet every 8 hours for the treatment of the "traveller's diarrhoea", it can be deduced from the aforesaid that the approved administration schedule does not guarantee a constant presence of rifaximin in the small intestine and therefore an optimal antibiotic activity.

It follows that any pharmaceutical composition comprising rifaximin which were able to release rifaximin with extended time of residence in the small intestine, would be considered an improvement to the therapeutic efficiency of rifaximin.

There thus exists the need for improved compositions able to release constant quantity of rifaximin, thereby maintaining a constant level of this antibiotic in plasma for a prolonged time.

BRIEF DESCRIPTION OF THE INVENTION

It has been surprisingly found that compositions containing rifaximin in a solid powder form obtained by a spray drying process with pharmaceutically acceptable excipients and optionally other ingredients, provides a controlled release of rifaximin and a long-lasting antibiotic effect in a patient.

Another aspect of the present invention is rifaximin powder obtained by a spray drying process. Said rifaximin powder is characterized by particular particle size distribution, porosity and surface area values as defined in the appended claims.

Another aspect of the invention is the spray-drying process used for preparing the rifaximin defined above, which is obtained using a solution of crystalline or amorphous rifaximin or their mixtures.

Another aspect of the invention is rifaximin obtained by spray drying for use as medicine.

Another aspect of the invention is composition rifaximin by spray drying—containing composition.

Another aspect of the invention is the composition containing rifaximin by spray draying for the treatment of pathologies like inflammatory disease and bacterial infections.

Another aspect of the invention is the composition containing rifaximin by spray drying for preventing pathologies like bacterial infections and the method of treatment in human and animal.

Another aspect of the invention of the invention is composition comprising other active ingredients and/or other forms of rifaximin.

DESCRIPTION OF THE FIGURES

FIG. 1: profile of plasma concentration after multiple administration of a 200 mg tablet of rifaximin of Example 3 and Normix® in the V7 subject.

FIG. 2: profile of plasma concentration after multiple administration of a 200 mg tablet of rifaximin of Example 3 and Normix® in the V11 subject.

FIG. 3: X-ray powder diffractogram of rifaximin obtained by spray drying process.

FIG. 4: $^{13}$C-NMR spectrum of rifaximin obtained by spray drying process.

FIG. 5: FT-IR spectrum of rifaximin obtained by spray drying process.

FIG. 6: X-ray diffraction spectrum of rifaximin obtained by milling process.

FIG. 7: PSD curve of rifaximin obtained by spray drying process.

FIG. 8: PSD curve of rifaximin obtained by milling process.

FIG. 9: SEM microscopy image of rifaximin obtained by spray drying process.

FIG. 10: SEM microscopy image of rifaximin by milling process.

DETAILED DESCRIPTION OF THE INVENTION

The present invention concerns rifaximin powder, a process for preparing the same, pharmaceutical compositions or pharmaceutical preparations comprising said rifaximin, and the use of these compositions and/or preparations for treating bowel diseases such as, for example, inflammatory bowel diseases, traveller's diarrhoea, IBS, SIBO, CD, hyperammonaemia therapy, hepatic encephalopathy, ulcerative colitis, enteritis, chronic pancreatitis, pancreatic insufficiency, colitis, diverticular disease, fibromyalgia, systemic lupus erythematosus and/or pouchitis.

Rifaximin is a compound represented by the formula

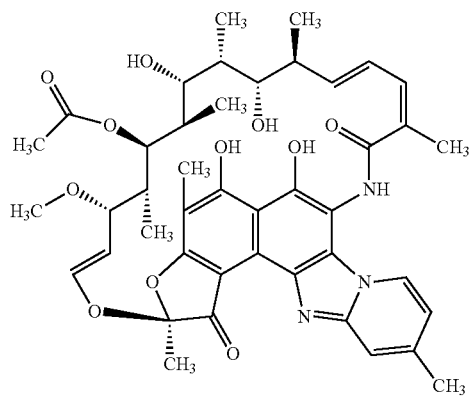

The present invention also concerns compositions containing 4-deoxy-4'-methyl-pyrido[1',2'-1,2] imidazo[5,4-c] rifamycin SV and 4-deoxy-pyrido [1',2':1,2] imidazo[5,4-c] rifamycin SV.

Rifaximin is approved and commercialized in several countries for the treatment of bowel infections, for the treatment of diarrhoea due to infection, for the prevention of post-surgical infections, for the treatment of hyperammonaemia and of hepatic encephalopathy. In particular in the USA, UK, Denmark and in Germany, rifaximin is approved for the treatment of bowel diseases called traveller's diarrhoea with a treatment schedule which foresees the administration of a 200 mg tablet three times a day for three days in a row.

Subjects affected by bowel diseases (BD), subjects suffering under active or acute diseases or syndromes and subjects in remission after one or more bowel diseases can benefit by a rifaximin treatment. The term bowel diseases includes, for example, irritable bowel syndrome (IBS), uncontrolled diarrhoea-associated Irritable Bowel Syndrome (dIBS), Crohn's disease, traveller's diarrhoea, ulcerative colitis, enteritis, small intestinal bacterial overgrowth, chronic pancreatitis, pancreatic insufficiency, colitis, diverticular disease, fibromyalgia, systemic lupus erythematosus or hepatic encephalopathy.

In particular, the subjects who can benefit by this treatment are those suffering from or being susceptible to forms of bowel diseases.

The term "rifaximin" indicates solvates and crystalline and amorphous forms of rifaximin. These polymorphous rifaximin forms are described in U.S. Pat. No. 7,045,620, US 2008/0262220, U.S. Pat. No. 7,612,199, US 2009/0130201 e in Cryst. Eng. Comm., 2008, 10 1074-1081.

The term "polymorphous/polymorphism" here indicates different crystalline forms of the compound in a hydrated state as property of some compounds and complexes, salts, solvates and amorphous.

A single compound can exist in a variety of polymorphic forms, which, though having the same molecular formula, have different physical properties, such as solubility, fusion temperature, hygroscopicity, size of particles, density and X-ray diffraction spectra. Moreover, the solubility of each polymorphous form can vary, thus varying also its bioavailability. That is the reason why the identification of pharmaceutical polymorphous forms is relevant for obtaining pharmaceutical forms with foreseeable solubility profiles. The polymorphic forms of a compound can be determined by X-ray diffraction spectroscopy and by means of other methods like IR spectroscopy.

The object of the present invention is represented by pharmaceutical composition comprising a rifaximin solid preparation specifically prepared for conferring improved solubility, the method for obtaining said rifaximin preparation, the pharmaceutical composition containing said rifaximin preparation suitable for guaranteeing a prolonged release in the time of rifaximin, the process for their preparation and the use in pathologies like bacterial infections and method of treatment.

The combination of properties of the rifaximin powder according to the invention and of the pharmaceutical composition comprising said rifaximin ensures that the composition, in particular in the form of tablets, releases rifaximin at predictable and controlled release. Advantageously the solid composition according to the invention maintains an effective rifaximin concentration in plasma during the treatment.

The composition contains rifaximin alone or in a mixture with other polymorphic forms of rifaximin to modulate the in vivo absorption.

Another aspect of the present invention is represented by the rifaximin solid preparation comprised in the pharmaceutical composition.

In a preferred aspect the composition for oral use is in the form of tablets or capsules containing an amount of rifaximin comprised between 20 and 800 mg. The amount of rifaximin in the pharmaceutical composition may thus be varied so as to obtain an amount suitable to achieve the desired therapeutic response in a patient, without causing any toxic effect on the subject.

For rifaximin a typical dose range is from 25 to 3000 mg per day, without causing any toxicity or other side effects. Rifaximin in pharmaceutical composition is administered at a concentration of about 1 mg to about 200 mg per kilogram of body of a patient.

The composition of the present invention provides by a high therapeutic effectiveness thanks to a longer time of permanence of the antibiotic activity in the site of infection.

The composition object of the present invention is useful in the treatment of human or animal subjects affected by bowel diseases or other diseases treatable with an antibiotic belonging to the rifamycin class, like rifaximin, or in the treatment of subjects who could benefit by the administration of said antibiotics, or who could be in danger of developing a bowel disease, or subjects in remission from a bowel disease, or subjects in relapse to bowel diseases, for instance subjects affected by immunosuppression, subjects exposed to bacterial infections, familiar with bowel syndromes, subjects suffering under hepatic damages, subjects with past episodes of HE.

Another aspect of the present invention is represented by methods of treating, preventing, or alleviating bowel related disorders comprising administering to a subject in need thereof an effective amount of solid dispersion compositions of rifaximin. Bowel related disorders include one or more of irritable bowel syndrome, diarrhoea, microbe associated diarrhoea, *Clostridium difficile* associated diarrhoea, travelers' diarrhoea, small intestinal bacterial overgrowth, Crohn's disease, diverticular disease, chronic pancreatitis, pancreatic insufficiency, enteritis, colitis, hepatic encephalopathy.

The length of treatment for a particular bowel disorder will depend in part on the disorder. For example, traveler's diarrhoea may only require treatment duration of 12 to about 72 hours, while Crohn's disease may require treatment durations from about 2 days to 3 months.

Rifaximin in pharmaceutical composition is useful for the prophylactic treatment for intestinal infections.

Rifaximin obtained by the process of the present invention can be used for the preparation of pharmaceutical composition without any limitation, such as vaginal infections or topical infections.

Pharmaceutical compositions of the present invention can be used to treat gastric dyspepsia, including gastritis, gastroduodenitis, antral gastritis, antral erosions, erosive duodenitis and peptic ulcers.

A particular aspect of the present invention is represented by pharmaceutical compositions in form of tablets comprising rifaximin obtained by spray drying with pharmaceutically acceptable excipients.

The pharmaceutical excipients can comprise, for example, one or more of a diluting agent, binding agent, lubricating agent, disintegrating agent, glidants, colouring agent, flavouring agent or sweetening agent. The composition may be formulated for selected coated and uncoated tablets, hard and soft gelatin capsules, sugar-coated pills, lozenges, wafer sheets, pellets, and powders in sealed packet. Solid composition are not limiting and rifaximin prepared by spray-draying may be formulated for topical use, for example, ointments, pomades, creams, gels and lotions, suspension in an aqueous or non-aqueous emulsion, elixir or syrup containing a predetermined amount of a rifaximin preparation by spray drying.

According to the invention rifaximin is administered to the subject by using a pharmaceutically acceptable composition that provides prolonged release the rifaximin to a subject.

Rifaximin powder according to the present invention is described in Example 1, wherein the present rifaximin is prepared by using a spray-drying technique starting from crystalline or amorphous forms of rifaximin, or from mixtures thereof. Said process allows to obtain solid powders having characteristics described below and in particular characteristic of amorphous form.

The starting crystalline or amorphous forms of rifaximin, or their mixtures, are charged in a spray drying apparatus, such as a fluid bed equipment, previously heated, such as, for instance, a Glatt GPCG 60, provided with e.g. an 18-inch Wurster system and a spraying nozzle, with an amount of organic solvent comprised between 1 and 40 liters per kg of rifaximin. The obtained suspension is then kept under stirring till complete dissolution of rifaximin.

Any suitable organic solvent can be used. For example alcohols C1-C4 can be used, ethanol or methanol being preferred.

The rifaximin containing solution is then sprayed inside the fluid bed apparatus at a pressure comprised between 0.5 and 2.5 bar under a flow of warm air. Then the solid rifaximin, dried until reaching constant weight at a temperature comprised between 20° C. and 120° C., preferably 35° C. and 110° C., and the formed particles are dried in a temperature range comprised between 20° C. and 120° C., preferably between 35° C. and 110° C., until reaching constant weight.

The solid powder obtained after drying is analyzed by X-ray diffraction spectroscopy. The X-ray diffractogram obtained does not show any peaks characterizing the cristallinity, as reported in the analytical characterization below.

FIG. 3 shows the X-ray diffractogram, FIG. 4 show the $^{13}$C-NMR spectrum, and FIG. 5 shows the FT-IR spectra of the rifaximin obtained by spay drying. The obtained rifaximin in powder form is stable after three months in a temperature range comprised between 30° C. and 40° C., with a humidity degree higher than 50%, which demonstrates that this active ingredient can be prepared and stored until its use.

A solid powder of rifaximin in a substantially amorphous form can be prepared also by a milling process, wherein the milling can be performed manually or automatically.

A rifaximin solid powder having characteristics of amorphous form obtained by spray drying was compared with a rifaximin solid powder obtained by milling. A comparative analysis of the X-ray diffractogram, particle size distribution (PSD), scanning electron microscope (SEM), specific surface area (BET), density and solubility, is reported in Example 2.

FIG. 3 and FIG. 6 show X-ray diffractograms of rifaximin obtained by spray drying and by milling, respectively. Both the solid forms are characterized by a non-crystalline profile in which the absence of sharp peaks indicates the presence of amorphous forms of rifaximin. The X-ray powder diffraction peaks in FIGS. 3 and 6 are distinct, and in particular rifaximin by spray drying is characterized by the halo-peaks with maximum at about 7.75°±0.2, 14.54°±0.2 and 18.33°±0.2, 2θ; rifaximin by milling is characterized by the halo-peaks with maximum at 7.44°±0.2, 14.40±0.2; 17.19±0.2, 2θ.

Figure 7:
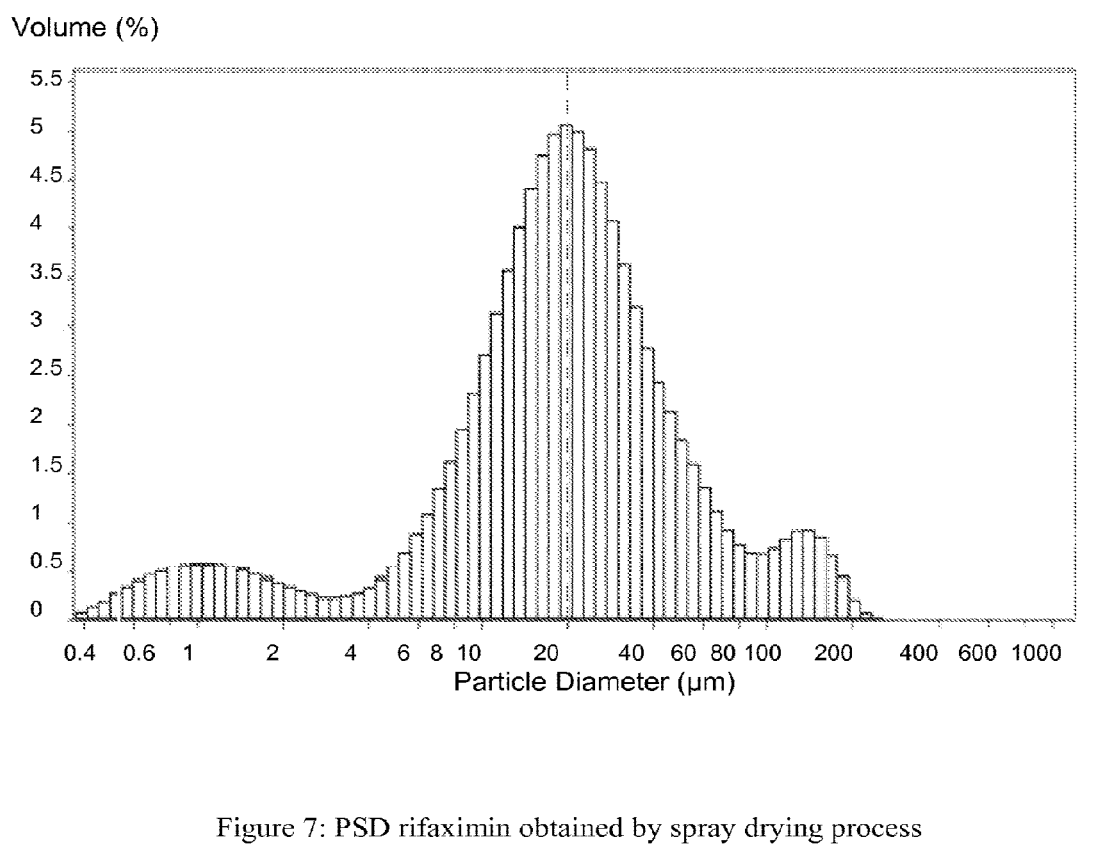

The particle size distribution (PSD) analysis shows that the solid form of rifaximin obtained by spray drying has a particles size distribution more homogeneous in respect to the rifaximin powder obtained by the milling process, as shown in FIG. 7 and in FIG. 8.

In particular, rifaximin prepared by spray drying is characterized by a substantially symmetric profile of the particle size distribution around 20 micrometers particles diameter, wherein the measure of $d_{90}$, (percentage of 90% of the particles diameter) is comprised between 40 and 120 micrometers, $d_{50}$ (percentage of 50% of the particles diameter) is comprised between 15 and 30 micrometers and $d_{10}$, (percentage of 10% of the particles diameter) is comprised between 2 and 10 micrometers. Rifaximin obtained by milling process is characterized by a non symmetric profile, wherein $d_{90}$ is comprised between 10 and 20 micrometers, $d_{50}$ is comprised between 6 and 12 micrometers, and $d_{10}$ is comprised between 0.5 and 4 micrometers.

Scanning electron microscopy (SEM) analysis shows that the rifaximin powder obtained by spray drying shows aggregates having dimension between about 10 μm and 40 μm, while SEM of rifaximin obtained by milling process shows aggregates having dimension between about 3 and 15 micrometers. Visual inspection of the images obtained and reported in FIG. 7 and FIG. 8 demonstrate these differences in the powder form.

Bulk density of rifaximin solid forms prepared by spray drying was measured in respect to the solid rifaximin by milling corresponding to their mass per unit volume. The bulk density measure of particles is an important physical characteristic of the pharmaceutical powder and the density of a solid depends on its assembly and therefore varies with the crystal structure and degree of crystallinity. In particular when a solid is amorphous or partially amorphous, its density may further depend upon the preparation, treatment and storage.

Three measures with three different samples were done for rifaximin by spray drying and for rifaximin by milling and the density calculated in grams per milliliter using a 10 ml volumetric flask.

The bulk density of rifaximin by spray drying is between 0.1 and 0.5 g/ml and the density of rifaximin by milling is between 0.3 and 0.6 g/ml.

The measure of specific surface area (BET) based on the physical absorption of inert gas, such as nitrogen on the rifaximin surface permits to show the difference in the particle size of rifaximin obtained by spray drying in respect to the rifaximin obtained by milling. From this technique it results that rifaximin by milling has a specific surface greater than rifaximin by spray drying. In particular BET of powder particle size of rifaximin by milling can range from 5 to 20 m$^2$/g, and more particularly between 9 to 12 m$^2$/g, while the BET of rifaximin by spray drying is between 0.01 to 10 m$^2$/g and more particularly between 5 to 8 m$^2$/g.

Comparative dissolution tests for rifaximin powders prepared by spray drying and by milling are reported in Example 2. The test was carried out in phosphate buffer at pH 6.8 at a temperature of 30±0.5° C. The results reported in Table 5 show that the rifaximin obtained by spray drying has a higher dissolution capacity if compared, for instance, to the rifaximin form prepared by milling and the concentration of solubilised rifaximin can range from 1.1 to 3 times with respect to the rifaximin obtained by milling.

The comparative analysis demonstrate that X-ray powder diffraction spectrum, PSD, BET, bulk density and solubility of rifaximin prepared by spray drying are features derived by the morphology of the powder, which in turn is determined by the preparation process.

The method of preparation of rifaximin by the spray drying process confers to the rifaximin preparation particular chemical-physical properties, different from other amorphous forms, such as for instance to the rifaximin obtained by means of a milling process.

The preparation of the tablets according to the present invention is carried out by means of a process comprising the steps of:

a) dry granulation of rifaximin obtained by a spray drying process, optionally mixed with rifaximin in crystalline form or in a mixture with other hydrate, solvate or amorphous form of rifaximin and/or in the presence of pharmaceutically acceptable excipients;

b) lubrication of the obtained granulate;

c) tabletting the granulate of step b) with pharmaceutically acceptable excipients;

d) optionally, preparation of coating varnish and coating of cores.

Example 3 describes a non limiting preparation of tablets comprising rifaximin obtained by a spray drying process.

The rifaximin powder obtained by spray drying is in form of granules. The granules are compressed in a Kilian machine, or an equivalent thereof, equipped with concave punches having different diameters according to the desired shape of the tablet with extra granule acceptable excipients.

The term "pharmaceutically acceptable excipients" includes, for instance, disgregants, lubricants, glidants, diluents, buffering agents, opacizer, plasticizer colouring flavouring.

The solid composition can comprise bioadhesive compounds providing bioadhesive properties.

Disgregants are selected among, for instance, cellulose derivatives such as sodium carboxymethylcellulose also called carmelose, cross-linked sodium carboxymethylcellulose also called croscarmelose, hydroxylpropyl methyl cellulose, hydroxylpropyl ethyl cellulose, hydroxylpropyl cellulose phthalate, polyvinyl acetate phthalate, povidone (polymer of polyvinylpirrolidone), copovidone (copolymer of polyvintpirrolidone), acrylic polymer and copolymer, polyvinyl acetate phthalate, poly vinyl acetate phthalate, or sodium starch glycolate and lubricants, such as for instance magnesium or calcium stearate, sodium stearyl fumarate, vegetable hydrogenated oils, mineral oils, polyethylene glycols, sodium lauryl sulfate, glycerides, sodium benzoate or their mixture.

Diluents are selected among cellulose, microcrystalline cellulose, calcium phosphate, starch, kaolin, hydrated calcium sulfate, calcium carbonate, lactose, sucrose, mannitol, glucose, glucans, xyloglucans, starches, such as corn starch and potato starch, powdered tragacanth, malt, gelatin.

The tablets can comprise glidants such as talc, cellulose microcrystalline or magnesium carbonate and lubricant such as magnesium or calcium stearate, glycerol distearate, glycerol dibenate.

The tablets can also comprise excipients, such as and natural oil, glycols, such as propylene glycol, polyols, such as glycerin, sorbitol, mannitol and polyethylene glycol, esters, such as ethyl oleate and ethyl laurate, buffering agents, such as magnesium hydroxide and aluminum hydroxide, alginic acid, pyrogen-free water; isotonic saline, ethyl alcohol, phosphate buffer solutions, and other non-toxic compatible substances employed in pharmaceutical formulations.

The tablets also can contain sweetening agents such as sucrose, sorbitol, mannitol, saccharine, acesulfame and neosperidin.

Colouring agents, release agents, coating agents, sweetening, flavouring and perfuming agents, preservatives and antioxidants can also be present in the compositions.

Preservative and antioxidants also can be included, such as ascorbic acid, cysteine hydrochloride, sodium bisulfate, sodium metabisulfite, sodium sulfite and metal chelating agents, such as citric acid, ethylenediamine tetraacetic acid (EDTA), sorbitol, tartaric acid, phosphoric acid.

Other excipients are polysaccharides such as starch, kitosan, chondroitin sulphate, dextran, guar gum, xyloglucan, xantanes or inulin and pectin, plasticizers such as, e.g. adipates, azelates, benzoates, citrates, phthalates, stearates and glycols, cellulose acetate, cellulose acetate butyrate, cellulose acetate propionate, ethyl cellulose, fat acids and their esters, waxes and zeins.

Optionally, hydrophilic polymers such as hydroxy ethyl and hydroxy propyl cellulose can be included.

The tablets can be coated with a film coating formed by filmogen agent such as microcrystalline cellulose, hydroxy methyl cellulose or hydroxy propyl cellulose, opacizer such as titanium dioxide, plasticizer such as propylene glycol or ethylene glycol and optionally colouring or flavouring substances.

To prolong the rifaximin residence time in the small intestine a dissolution profile comprised between 5% and 90% is considered appropriate. In order to achieve this objective a special granulation technology was used. In pharmaceutical technology the method most frequently used by the persons skilled in the art is the wet granulation method, which is adopted when the intent is to favour the dissolution of poorly soluble compounds.

The use of the of the known techniques would have produced the transformation of the amorphous form to other forms with the risk to have a complete dissolution or dissolution at concentrations lower than 5% (Cryst. Eng. Comm., 2008, 10, 1074-1081).

On the contrary, by adopting a dry granulation technique it was possible to prevent such transformation and to obtain tablets characterized by a dissolution corresponding to a value comprised between 5% and 90% of the rifaximin contained in the composition, according to the requirements described in European Pharmacopoeia Ed. 6.0 pp. 266-275.

In a particular aspect, pharmaceutical compositions in tablets comprising rifaximin in solid form obtained by spray drying process, comprise one or more disgregant, one or more glidants, one or more diluents wherein rifaximin can range between 10-90% by weight of the solid composition.

The preferred composition comprise rifaximin in an amount between 30 to 70% by weight, lubricant between 2 to 5% by weight; disgregant between 3 to 8% by weight; diluent between 5 to 65% by weight; glidants between 0.1 to 2% by weight to the finished composition and optionally flavouring and colouring agent.

In the preferred composition of the invention the disgregant are selected among sodium carboxymethylcellulose, cross-linked carboxymethylcellulose, copovidone, sodium starch glycolate.

Diluents are selected among microcrystalline cellulose, lactose, cellulose and mannitol.

The lubricant is selected between glycerol distearate and glycerol dibenate.

The glidants is selected among talc, silica and colloidal anhydrous silica.

Tablets can be coated with a film coating comprising opacizers, colouring agents, plasticizers and flavouring agents.

Table 7 reports the dissolution profile of the tablets of the present invention, comprising rifaximin prepared by spray drying in comparison with commercial rifaximin tablets, named a Normix® tablet. The new solid composition resulting from the combination of the amorphous form of rifaximin, the morphology of the powder obtained by the spray drying method of preparation, and the solid pharmaceutical composition in form of tablets, shows the unexpected result of obtaining a pharmaceutical composition able to provide prolonged release of the rifaximin active ingredient. The pharmaceutical composition in form of tablets comprising 200 mg of rifaximin, as in Example 3, is able to allow a longer time of residence of rifaximin in human organs, where it carries on its pharmacological action longer, if compared with the commercially available preparations of rifaximin, without remarkably increasing the levels of plasmatic absorption, which is a relevant aspect for limiting the side effects and/or adverse events.

The PK profile indicates that this new formulation, by providing effective concentrations of rifaximin in-vivo, is able to guarantee a better therapeutic action in case of oral administration of a 200 mg tablet three times a day.

This evidence is shown in Example 4, which reports a pharmacokinetic study using tablets prepared according to Example 3, containing rifaximin obtained by spray drying as described in Example 1. The study has been carried out in comparison with the commercial formulation Normix® containing a crystalline rifaximin like the polymorph of rifaximin-α. A group of 24 healthy volunteers, whose demographic data are reported in Table 8 and Table 9, received one or two 200 mg tablets of rifaximin prepared as described in Example 3 in comparison with an equivalent number of 200 mg tablets of Normix®.

Table 10 reports the plasma concentrations of rifaximin expressed in nanograms per blood milliliter, measured over time in humans after the oral administration of a 200 mg tablet of rifaximin prepared as in Example 4. Table 11, on the other hand, reports the corresponding values obtained when a 200 mg tablet of commercially available rifaximin, namely Normix®, was administered.

The comparison of the data shows that the 200 mg tablets of rifaximin prepared according to Example 3, lengthen the time interval wherein rifaximin is detectable in the plasma if compared with the commercially available tablets. Example 4 reports PK comparative data in subjects who received a single oral 200 mg dose, or two 200 mg doses of composition comprising rifaximin from spray drying of Example 3, in respect to a single oral 200 mg dose or two 200 mg doses of commercial tablets. The results demonstrate that commercial preparation rifaximin is no longer detectable in the plasma 4 hours after the administration in most subjects, and is no longer detectable in the plasma 6 hours after the administration in all subjects (Table 11), while composition comprising rifaximin from spray drying according to the present invention is detected in the plasma in nearly all subjects 4 hours after the administration (10/12), in most subjects (7/12) even 8 hours after the administration, and in some subjects even up to 16 hours after the administration.

In the case of an administration of two 200 mg tablets of rifaximin with the preparation of Example 3, most subjects (10/12) show remarkable amounts of rifaximin 12 hours, and some subjects even up to 24 hours, after the administration.

These results are associated to the fact that the absolute plasma concentration does not exceed about 15 ng/ml with the administration of one 200 mg tablet, and 100 ng/ml with the administration of two 200 mg tablets.

By administering the same amount of Normix®, a few subjects show detectable plasma concentrations of rifaximin just 6 hours after the administration, and no subject shows them 12 hours after the administration.

Under these conditions, the most suitable dosage for the tablets comprising rifaximin prepared by spray drying is three 200 mg tablets of rifaximin three times a day, as e.g. prescribed in the treatment of the travellers' diarrhoea. In fact, this posology guarantees a better antibiotic effect of rifaximin for the subject. To this regard and for exemplificative purposes only, FIG. 1 and FIG. 2 show the calculated PK profiles in the hypothesis of repeated doses of three 200 mg tablets of rifaximin three times a day, for the subjects V7 and V11, on the basis of the values obtained in Table 10 and Table 11.

Solid preparation in the form of tablets of Example 3 comprising rifaximin obtained by spray drying, guarantee a more constant presence of rifaximin, though maintaining limited maximum concentrations in the plasma and producing a limited drug accumulation during the therapy.

The effect of limitation of maximum concentration of rifaximin in the plasma is the result of the tablet composition, of the adopted pharmaceutical form and of the preparation method of the pharmaceutical form. In fact, Table 16 of Example 5 reports the PK parameters obtained in dogs when only the rifaximin prepared according to Example 1, without any additional excipient, is administered to the animal. In order to compare these data with the values obtained after the administration to humans, reported in Table 14 of the Example 3, the different species, human and canine, and the different dosages must be taken in account.

With regard to the species, it is known that it is possible to compare bioavailability data in human and canine species, as described by Dressmann J. B. in Pharm. Res. 4, 123-31, 1986, since the physiology of the stomach in the two species is quite similar. However, humans and dogs show a different pH in the small intestine, which in humans is about 5, whereas in dogs is about 7. This difference could affect the bioavailability if it were relevant for the solubility of the compound.

In the case of rifaximin, however, this difference is not relevant since a pH variation between 5 and 7 does not affect the solubility of rifaximin, as shown in Example 6.

Another observed difference between human and canine species is the shorter intestinal transit time in dogs, which could conceivably result in a lower fraction adsorbed for drugs.

The different bioavailability factors in human and canine species have been taken in account by adopting the conversion factor from dog doses to human equivalent doses (HED) of 0.54, as reported in the FDA Guidance-for-Industry. In Example 5, having the dogs received a dose of 100 mg/kg, it corresponds to 54 mg/kg HED.

The human subjects of the patients studied who had received a 200 mg tablet of rifaximin, had a mean body weight of 67.67 kg, as shown in Table 8, therefore they received an average of 2.9 mg/kg of rifaximin, namely a 18.6-folds lower amount of rifaximin than the HED administered to the dogs. The PK parameters, therefore, could be expected to be proportionally reduced by about the same factor, as shown in Table 1.

TABLE 1

Comparison of PK values dog-man receiving rifaximin - Mean values ± standard error

| | $C_{max}$ (ng/ml) | $T_{max}$ (h) | $AUC_{0-24\,h}$ (ng · h/ml) |
|---|---|---|---|
| Values observed in dogs after administration of 100 mg/kg (Table 14) corresponding to a HED of 54.4 mg/kg | 1044.1 ± 588.46 | 2 | 2854.31 ± 1489.87 |
| Values calculated in humans proportionally reduced to the dosage 2.9 mg/kg | 56.1 ± 31.63 | ND | 143.4 ± 80.10 |
| Values observed in humans after administration of 200 mg tablets corresponding to 2.9 mg/kg | 3.70 ± 0.55 | 1.04 | 11.47 ± 2.35 |

By comparing the values of PK parameters calculated at 2.9 mg/kg HED obtained on the basis of the experiment on dogs with those observed on humans, when the rifaximin of Example 1 is comprised in the pharmaceutical preparation of Example 3, it results that the new composition, by combining the effect of the form of rifaximin and pharmaceutical composition, as described in Example 3, reduces the bioavailability levels of rifaximin in blood if compared to a direct administration of the rifaximin prepared by the spray-drying method, as described in Example 1.

The pharmaceutical composition in tablets obtained according to Example 3 shows indeed the unexpected result derived from the combination of parameters working in opposite ways: the rifaximin produced by the spray drying process leads to more soluble rifaximin with a possible increase of bioavailability, whereas the composition and the pharmaceutical form in tablets and the production method limits the absorption level, giving as a result a controlled release.

The evidence of the property of the formulation is shown in FIGS. 1 and 2, reporting the values of plasma concentrations in two different volunteers, calculated after repeated administrations of formulations in tablets containing the rifaximin prepared according to Example 3 if compared with the commercial product Normix®.

The comparison of the two profiles in the two healthy volunteers treated with the formulation of the present invention demonstrates that no time interval over the whole therapy shows any rifaximin detectable in the plasma, whereas the patients treated with the commercially available tablets containing rifaximin (Normix®) show non-analytically detectable plasma concentrations of rifaximin.

Therefore an aspect of the invention is a composition able to release rifaximin at predictable and controlled release.

Such composition comprises a rifaximin powder having the morphological feature described above, which are obtained by a spray drying process.

Another aspect of the present invention is represented by pharmaceutical formulations containing rifaximin in solid form in an amount comprised between 10 and 800 mg in a solid preparation with acceptable excipients.

Another aspect of the invention is a rifaximin powder having the morphological features described above, prepared by spray draying, and associated with acceptable excipients known to the skilled in the art, for use as topical administration such as ointment, cream lavage, foam.

Another aspect of the invention is rifaximin powder having the morphological features described above, prepared by spray draying, and associated with acceptable excipients known to the skilled in the art, for use as oral administration as suspension, syrup or mouth wash.

A further aspect of the present invention are pharmaceutical compositions able to produce plasma concentrations of rifaximin higher than 0.5 ng/ml in the blood of humans 4-12 hours after the administration of an amount of rifaximin not lower than 200 mg in the form of tablets.

A further aspect of the present invention is a pharmaceutical composition containing rifaximin obtained by spray drying, able to produce plasma concentrations of rifaximin higher than 0.5 ng/ml in the blood of humans 6-24 hours after the administration of an amount of rifaximin not lower than 400 mg in the form of tablets.

A further aspect of the present invention is a formulation of rifaximin that, with an administration of 200 mg of rifaximin, produces a maximum concentration of rifaximin in the blood lower than about 15 ng/ml.

A further aspect of the present invention is a pharmaceutical composition comprising rifaximin that, with an administration of 200 mg, produces a maximum concentration of rifaximin in the blood lower than about 100 ng/ml.

A further aspect of the present invention is the use of the formulation in the treatment of bacterial bowel infections.

A further aspect of the present invention is a packaged composition comprising a therapeutically effective amount of rifaximin having the morphological features described above, prepared by spray drying, and a pharmaceutically acceptable carrier or diluent, wherein the composition is formulated for treating a subject suffering from or susceptible to a bowel disorder, and packaged with instructions to treat a subject suffering from or susceptible to a bowel disorder.

Kits are also provided herein, for example, kits for treating a bowel disorder in a subject. The kits may contain, for example, one or more of the solid dispersion forms of rifaximin having the morphological features described above, prepared by spray drying, and instructions for use. The instructions for use may contain proscribing information, dosage information, storage information, and the like.

Rifaximin can be administered at dosage higher than 2500 mg/day without any side effect and the rifaximin composition can be administered at a concentration of about 1 mg to about 200 mg per kilogram of body weight.

The pharmaceutical composition can be administered in combination with other therapy treatment.

The following non-limiting examples of the invention are provided.

Example 1

Method of Preparation of a Rifaximin Powder by Spray Drying

In a fluid bed equipment Glatt GPCG 60, provided with an 18-inch Wurster system and a 1.8 mm spraying nozzle, 40 kg of rifaximin-α are charged and then added with 457.2 liters of 96% ethanol (v/v). The suspension so formed is kept under stirring till complete dissolution of rifaximin.

The ethanol solution is sprayed inside the fluid bed under a pressure comprised between 1.0 and 1.5 bar through the 1.8 mm nozzle under a previously heated flow of heated air. At the end of the spraying phase the solid rifaximin powder is further dried to remove the excess solvent.

The conditions adopted for the spraying process are described in detail in Table 2.

TABLE 2

| Process parameters | Preheating | Spraying | Drying |
|---|---|---|---|
| Inlet air volume | 800 ± 200 m³/h | 800 ± 200 m³/h | 800 ± 200 m³/h |
| Inlet air temperature | 90 ± 10° C. | 90 ± 10° C. | 60 ± 5° C. |
| Spray pressure | | 0.7 ± 0.2 Bar | |
| Spray rate | | 50-380 g/min | |
| Product temperature | | 55-70° C. | 50 ± 2° C. |

The obtained rifaximin powder is analyzed by X-ray spectroscopy, $^{13}$C-NMR spectrometry and IR spectroscopy and is stable at a temperature of 40° C.+2 with a relative humidity of 75% up to three months.

X-ray diffraction spectrum is reported in FIG. 3 who shows halo-peaks having maximum at 7.75°±0.2, 14.54°±0.2 and 18.33°±0.2, 2θ.

X-ray diffraction spectrum are obtained by the Bragg-Brentano geometry under the following conditions: X-ray pipe: copper; radiation: K(α1), K(α2); generator current tension: KV 40, mA 40; monochromator: graphite; step size: 0.02; step time: 1.25 seconds; initial and final angular value of 2θ: 3.0°-30°±0.2 d.

FIG. 4 shows the $^{13}$C-NMR spectrum obtained by the Varian 400 instrument at 100.56 MHz, by melting the sample in chloroform having a purity higher than 99.8% and containing tetramethylsilane as internal standard.

FIG. 5 reports the IR spectrum obtained with the Spectrum One equipment, Perkin Elmer, by using a 0.5% dispersion of rifaximin in potassium bromide and the spectrum is recorded at frequencies of 4000 to 450 cm$^{-1}$.

The so obtained rifaximin is stable, as shown in Table 3.

TABLE 3

Rifaximin obtained from Example 1 and kept at T = 40° C. ± 2° C. with relative humidity = 75 ± 5%

| Test | Acceptance criteria | T0 | 1 month | 3 months |
|---|---|---|---|---|
| Description | Red-orange powder | Red-orange powder | Red-orange powder | Red-orange powder |

TABLE 3-continued

Rifaximin obtained from Example 1 and kept at T = 40° C. ± 2° C. with relative humidity = 75 ± 5%

| Test | Acceptance criteria | T0 | 1 month | 3 months |
|---|---|---|---|---|
| FT-IT Spectrum | Complies with standard | Complies with standard | Complies with standard | Complies with standard |
| X-Ray diffraction spectrum | Complies with an amorphous form of Rifaximin | Complies with an amorphous form of Rifaximin | Complies with an amorphous form of Rifaximin | Complies with an amorphous form of Rifaximin |
| Water content (Karl Fisher) | ≤8% | 2.2% | 4.9% | 5.4% |
| Total impurities | ≤2.0% | 0.51% | 0.54% | 0.95% |

Example 2

Comparative Analysis Between Rifaximin Obtained by Spray Drying and by a Milling Process a) X-ray Analysis The X-ray diffraction spectrum are obtained by the Bragg-Brentano geometry under the following conditions: X-ray pipe: copper; radiation: K($\alpha$1), K($\alpha$2); generator current tension: KV 40, mA 40; monochromator: graphite; step size: 0.02; step time: 1.25 seconds; initial and final angular value of 2 $\theta$:3.0°-30°±0.2.

FIG. 3 and FIG. 6 report respectively X-ray spectrum of rifaximin obtained by spray drying and by milling.

X-ray diffraction spectrum of rifaximin obtained by spray draying process is characterized by halo-peaks having maximum at 7.75°±0.2, 14.54°±0.2 and 18.33°±0.2, 2$\theta$.

X-ray diffraction spectrum of rifaximin obtained by milling process is characterized by halo-peaks having maximum at 7.44±2$\theta$, 14,40±2$\theta$; 17.19±2$\theta$.

b) Particle Size Dimension (PSD)

The particle size analysis were performed using Beckman—Coulter LS100 Q particle size analyzer equipped with a micro-volume cell. The solvent used is White Spirit (WS).

In Table 4 are reported the average size of the particles obtained with spray drying and milling processes.

A percentage corresponding to 10% (d10) of the total particles has an average size of 4.56 µm for spray drying and 1.84 for milling; a percentage corresponding to 50% (d50) of the total particles has an average size of 19.60 µm for spray drying and 8.17 for milling; a percentage corresponding to 90% (d90) of the total particles has an average size of 62.21 µm for spray drying and 12.92 for milling;

TABLE 4

| | Diameter Particle (µm) Spray Drying Process | Diameter Particle (µm) Milling Process |
|---|---|---|
| $d_{10}$ | 4.56 | 1.84 |
| $d_{50}$ | 19.60 | 8.17 |
| $d_{90}$ | 62.21 | 12.92 |

FIG. 7 and FIG. 8, show the particle size profile of rifaximin obtained by spray drying process and milling process respectively.

c) SEM Microscopy

The samples were analyzed by SEM and the results are reported in FIG. 9 and in FIG. 10, respectively, for rifaximin amorphous forms obtained by spray drying and milling.

Rifaximin prepared by spray drying shows aggregates having dimension between 10 and 40 µm and the powder presents porous characteristics and a defined profile; solid rifaximin by milling shows aggregates having dimension between 3 and 15 µm and the powder presents porous characteristics and a spherical profile.

d) Bulk Density

Three measures with three different samples were done for rifaximin by spray drying and for rifaximin by milling and the density calculated in grams per milliliter using a 10 ml volumetric flask.

The density of rifaximin by spay drying is 0.257 g/ml and the density of rifaximin by milling is 0.327 g/ml.

e) Specific Surface Area (BET)

For the determination of low surface areas a flowing gas technique was used. The analysis were performed using nitrogen gas on 300 mg of sample died under vacuum, increasing the temperature from 25° C. to 100° C. with a heating rate of 10° C./min. The specific surface area of rifaximin by spray drying is between 0.01 and 5 m$^2$/g and the specific surface area of rifaximin by milling is between 6 and 12 m$^2$/g.

f) Solubility

500 Mg of each preparation of rifaximin reported in Example 1 and rifaximin by milling, respectively, were separately suspended in 750 ml of an aqueous buffer solution of phosphates, pH 6.8, temperature 30±0.5° C.

The solutions containing suspended rifaximin are stirred by means of a sweep stirrer for 150 minutes at the stirring rate of 250 rpm. Samples taken at 5-minute intervals during the first hour and at 15-minute intervals in the remaining time, are analysed in HPLC after filtration. The results are reported in Table 5.

TABLE 5

Solubility over time of rifaximin preparation

| Time (min) | Concentration (mg/l) | |
|---|---|---|
| | Spray drying | Milling |
| 5 | 14.4 | 10.8 |
| 10 | 30.2 | 14.3 |
| 15 | 44.0 | 15.9 |
| 20 | 47.0 | 16.7 |
| 25 | 38.0 | 16.9 |
| 30 | 28.7 | 16.7 |
| 35 | 22.4 | 16.1 |
| 40 | 17.7 | 15.4 |
| 45 | 14.9 | 14.8 |
| 50 | 13.1 | 14.0 |
| 55 | 11.8 | 13.5 |
| 60 | 11.0 | 12.9 |
| 75 | 9.9 | 12.1 |
| 90 | 9.5 | 10.9 |
| 105 | 9.3 | 9.8 |
| 120 | 9.1 | 9.0 |
| 135 | 9.0 | 8.3 |
| 150 | 8.8 | 7.9 |

Example 3

Preparation of rifaximin in tablets

The preparation of the tablets containing 200 mg of rifaximin comprises the following steps:
a. Preparation of rifaximin powder by spray drying as described in Examples 1;
b. Dry granulation by compaction;
c. Lubrication of granulate;
d. Tabletting;
e. Preparation of coating varnish;
f. Coating of cores.

A tablet contains the amounts reported in Table 6.

TABLE 6

Composition of a 200 mg tablet

| Drug Substance | Amount (mg) | % (w/w) |
|---|---|---|
| Powder Rifaximin | 200.00 | 55.97 |
| Sodium starch glycolate | 15.00 | 4.20 |
| Glycerol distearate | 18.00 | 5.04 |
| Colloidal anhydrous silica | 1.00 | 0.28 |
| Talc | 1.00 | 0.28 |
| Microcrystalline cellulose | 115.00 | 32.18 |
| Hydroxy propyl methyl cellulose | 5.15 | 1.44 |
| Titanium dioxide | 1.50 | 0.42 |
| Disodium edetate | 0.02 | $5.60 \times 10^{-3}$ |
| Propylene glycol | 0.50 | 0.14 |
| Iron oxide E172 | 0.15 | 0.04 |

Sodium starch glycolate, glycerol distearate, talc and microcrystalline cellulose are weighted in the respective amounts reported in Table 6 and passed through a 0.8 mm sieve. They are then put in a V-type powder mixer and the mixture is stirred for at least 30 minutes.

The powder mixture is put with the respective amount of rifaximin, into a hopper of the continuous compacting-granulating machine, which produces a granulate of the desired calibration.

The granulate is then added with glycerol distearate, talc, microcrystalline cellulose, colloidal anhydrous silica, all being previously passed through a 0.5 mm sieve. Colloidal anhydrous silica and microcrystalline cellulose are premixed before sieving. The mixture is then put back in the mixer and mixed for 7 minutes. The granulate is compressed by means of a rotative tabletting machine Kilian or equivalent equipped with concave punches with a 10 mm diameter to obtain the tablets. The coating procedure is performed in an appropriate room under microclimatic control.

Tablets are heated at range 41° C.-43° C. by warm air, and the film coating is sprayed on the tablets. At the end of coating phase tablets are dried at range 41° C.-43° C. by warm air for 30 min.

The disintegration time of the tablets coming from the above mentioned manufacturing process was of 5 minutes by performing the test in accordance with Ph. Eur. conditions, Ed. 6.3, no. 20901 pp. 3943-3945.

The measured dissolution rate of the tablets, evaluated by performing a dissolution test in accordance with Ph. Eur. conditions, Ed. 6.0, no. 20903, pp. 266-275, by introducing a tablet in 1000 ml phosphate buffer 0.1 M at pH 7.4 at a temperature of 37±0.5° C., rotation speed 100 rpm, is shown in Table 7.

The rifaximin released by the thus prepared tablets was analysed and compared with the commercially available Normix® tablets containing rifaximin-α. The amount of rifaximin released in the phosphate buffer was determined by wavelength spectrophotometry corresponding to 293±2 nm in comparison with a reference solution of rifaximin. The amounts of rifaximin released up to 180 minutes are reported in Table 7.

TABLE 7

Dissolution profile of the tablets

| Time (min) | 200 mg rifaximin as described in Example 3 | 200 mg commercial rifaximin (Normix ®) containing rifaximin-α |
|---|---|---|
| 0 | 0.0 | 0.0 |
| 15 | 4.1 | 2.5 |
| 30 | 9.3 | 2.8 |
| 45 | 12.5 | 2.8 |
| 60 | 17.0 | 3.1 |
| 90 | 19.4 | 3.2 |
| 120 | 23.0 | 3.1 |
| 180 | 27.2 | 2.7 |

Example 4

Randomized Crossover Study for the Evaluation of Safety and of PK Profile of a Single Oral 200 Mg Dose or Two 200 Mg Doses of Rifaximin Tablets as Obtained in Example 3 in Comparison with a Single Oral 200 Mg Dose of Normix® or Two 200 Mg Doses in Healthy Human Volunteers In the fasted state, 12 healthy volunteers whose demographic data are reported in Table 7, received in crossover a tablet containing 200 mg of rifaximin described in Example 3 or a 200 mg tablet of Normix®, and 12 healthy volunteers, whose demographic data are reported in Table 9, received two 200 mg tablets of rifaximin described in Example 3 or two 200 mg tablets of Normix®.

Each subject received each of the two rifaximin preparations separated by an interval of one week.

TABLE 8

Demographic parameters of the subjects who have received one 200 mg tablet of rifaximin of Example 3

|      | Age (years) | Height (cm) | Weight (kg) | BMI   |
|------|-------------|-------------|-------------|-------|
| Mean | 36.67       | 169.25      | 67.67       | 23.50 |
| SD   | 8.53        | 9.35        | 11.65       | 2.71  |
| CV % | 23.27       | 5.53        | 17.22       | 11.55 |
| Min  | 27.00       | 153.00      | 52.00       | 19.00 |
| Max  | 51.00       | 180.00      | 86.00       | 27.00 |

TABLE 9

Demographic parameters of the subjects, who have received two 200 mg tablets of rifaximin of Example 3

|      | Age (years) | Height (cm) | Weight (kg) | BMI   |
|------|-------------|-------------|-------------|-------|
| Mean | 37.67       | 169.83      | 72.75       | 25.08 |
| SD   | 8.30        | 7.41        | 11.23       | 2.91  |
| CV % | 22.05       | 4.36        | 15.44       | 11.59 |
| Min  | 21.00       | 158.00      | 50.00       | 20.00 |
| Max  | 51.00       | 186.00      | 90.00       | 30.00 |

The study determined the bioavailability of the two rifaximin preparations by measuring the plasma concentration of rifaximin over time after oral administration.

The blood samples, respectively taken 0; 0.5; 1; 1.5; 2; 3; 4; 6; 8; 10; 12; 16; 24 hours after the administrations, were analysed by a LC-MS/MS method having a limit of quantization of 0.5 ng/ml and the results are shown in Table 10 and in Table 11 for the administration of a 200 mg tablet of rifaximin of Example 3 and of Normix®, respectively. In Table 12 and in Table 13 the values corresponding to the administration of two 200 mg tablets of rifaximin of Example 3 and Normix® are reported.

TABLE 10

PLASMA CONCENTRATION OF RIFAXIMIN (NG/ML) AFTER ORAL ADMINISTRATION OF A 200 MG RIFAXIMIN TABLET PREPARED ACCORDING TO EXAMPLE 3

| Time (h) | V1   | V2   | V3   | V4   | V5   | V6   | V7   | V8   | V9   | V10  | V11  | V12  |
|----------|------|------|------|------|------|------|------|------|------|------|------|------|
| 0        | n.e. | n.e. | n.e. | n.e. | n.e. | n.e. | n.e. | n.e. | n.e. | n.e. | n.e. | n.e. |
| 0.5      | 3.76 | n.e. | 0.67 | 2.40 | 1.77 | 1.43 | 0.99 | 4.48 | 2.60 | 0.64 | 1.44 | 0.55 |
| 1        | 2.40 | n.e. | 5.49 | 4.00 | 1.47 | 2.25 | 1.04 | 3.71 | 2.02 | 1.47 | 3.37 | 0.97 |
| 1.5      | 1.41 | n.e. | 3.85 | 3.61 | 1.14 | 2.06 | 6.39 | 2.57 | 1.56 | 1.37 | 4.99 | 1.31 |
| 2        | 1.16 | n.e. | 2.32 | 2.11 | 0.78 | 1.14 | 4.10 | 1.93 | 1.25 | 1.43 | 7.32 | 2.98 |
| 3        | 0.99 | n.e. | 1.46 | 1.48 | n.e. | 1.17 | 2.84 | 1.04 | 0.89 | 1.16 | 4.03 | 2.08 |
| 4        | 1.19 | n.e. | 0.96 | 1.13 | n.e. | 0.82 | 2.60 | 0.73 | 0.71 | 0.75 | 2.88 | 1.51 |
| 6        | 1.36 | n.e. | 0.71 | 1.24 | n.e. | 1.15 | 1.47 | 0.52 | 0.93 | n.e. | 1.89 | 0.88 |
| 8        | 0.80 | n.e. | n.e. | 0.98 | n.e. | 0.64 | 1.14 | n.e. | 0.57 | n.e. | 1.43 | 0.60 |
| 10       | 0.54 | n.e. | n.e. | 0.63 | n.e. | n.e. | 0.79 | n.e. | n.e. | n.e. | 0.78 | 0.51 |
| 12       | n.e. | 1.83 | n.e. | 0.61 | n.e. | n.e. | 0.73 | n.e. | n.e. | n.e. | 0.75 | n.e. |
| 16       | n.e. | n.e. | n.e. | n.e. | n.e. | n.e. | n.e. | n.e. | n.e. | n.e. | 0.60 | n.e. |
| 24       | n.e. | n.e. | n.e. | n.e. | n.e. | n.e. | n.e. | n.e. | n.e. | n.e. | n.e. | n.e. | n.e. = not evaluable, because lower than the detectable limit of the method.

TABLE 11

PLASMA CONCENTRATION OF RIFAXIMIN (NG/ML) AFTER ORAL ADMINISTRATION OF A 200 MG RIFAXIMIN TABLET OF NORMIX ®

| Time (h) | V1   | V2   | V3   | V4   | V5   | V6   | V7   | V8   | V9   | V10  | V11  | V12  |
|----------|------|------|------|------|------|------|------|------|------|------|------|------|
| 0        | n.e. | n.e. | n.e. | n.e. | n.e. | n.e. | n.e. | n.e. | n.e. | n.e. | n.e. | n.e. |
| 0.5      | n.e. | n.e. | 2.06 | 0.68 | 0.70 | n.e. | 3.00 | 1.04 | 1.27 | n.e. | 0.76 | 0.67 |
| 1        | 1.55 | 0.53 | 1.88 | n.e. | 1.44 | 0.53 | 4.95 | 0.76 | 2.07 | 0.50 | 0.94 | 1.85 |
| 1.5      | 1.04 | 0.54 | 1.01 | n.e. | 0.98 | n.e. | 0.85 | 0.53 | 1.63 | 0.53 | 1.70 | 1.38 |
| 2        | 0.79 | n.e. | 0.71 | n.e. | 0.93 | n.e. | 1.11 | n.e. | 0.93 | 0.68 | 0.90 | 1.08 |
| 3        | 0.53 | n.e. | n.e. | n.e. | 0.55 | n.e. | n.e. | n.e. | 1.10 | 0.68 | 0.80 | 0.69 |
| 4        | n.e. | n.e. | n.e. | n.e. | n.e. | n.e. | n.e. | n.e. | 0.72 | 0.61 | 0.58 | n.e. |
| 6        | 0.59 | n.e. | n.e. | n.e. | n.e. | n.e. | n.e. | n.e. | n.e. | n.e. | n.e. | n.e. |
| 8        | n.e. | n.e. | n.e. | n.e. | n.e. | n.e. | n.e. | n.e. | n.e. | n.e. | n.e. | n.e. |
| 10       | n.e. | n.e. | n.e. | n.e. | n.e. | n.e. | n.e. | n.e. | n.e. | n.e. | n.e. | n.e. |
| 12       | n.e. | n.e. | n.e. | n.e. | n.e. | n.e. | n.e. | n.e. | n.e. | n.e. | n.e. | n.e. |
| 16       | n.e. | n.e. | n.e. | n.e. | n.e. | n.e. | n.e. | n.e. | n.e. | n.e. | n.e. | n.e. |
| 24       | n.e. | n.e. | n.e. | n.e. | n.e. | n.e. | n.e. | n.e. | n.e. | n.e. | n.e. | n.e. | n.e. = not evaluable, because lower than the detectable limit of the method.

TABLE 12

PLASMA CONCENTRATION OF RIFAXIMIN (NG/ML) AFTER
ORAL ADMINISTRATION OF TWO 200 MG RIFAXIMIN
TABLETS PREPARED ACCORDING TO EXAMPLE 3

| Time (h) | V13 | V14 | V15 | V16 | V17 | V18 | V19 | V20 | V21 | V22 | V23 | V24 |
|---|---|---|---|---|---|---|---|---|---|---|---|---|
| 0 | n.e. | n.e. | n.e. | n.e. | n.e. | n.e. | n.e. | n.e. | n.e. | n.e. | n.e. | n.e. |
| 0.5 | 4.55 | 1.10 | 1.92 | 3.03 | n.e. | 2.23 | 10.48 | 30.19 | 13.69 | 18.73 | 2.01 | 2.82 |
| 1 | 12.16 | 1.80 | 4.08 | 6.04 | 3.77 | 5.16 | 10.43 | 23.33 | 14.26 | 57.19 | 1.43 | 15.23 |
| 1.5 | 8.79 | 2.11 | 3.39 | 3.73 | 4.35 | 5.04 | 6.35 | 20.02 | 18.20 | 53.66 | 1.26 | 16.25 |
| 2 | 4.90 | 2.17 | 3.39 | 2.69 | 3.99 | 5.78 | 5.07 | 15.47 | 20.66 | 32.13 | 0.97 | 20.61 |
| 3 | 3.28 | 1.63 | 3.61 | 1.55 | 4.42 | 5.26 | 3.44 | 9.52 | 24.89 | 18.84 | 0.72 | 9.25 |
| 4 | 2.20 | 1.14 | 4.20 | 1.26 | 3.34 | 4.13 | 3.77 | 5.69 | 24.89 | 12.89 | 0.55 | 4.99 |
| 6 | 3.19 | 0.85 | 2.71 | 1.78 | 3.36 | 2.41 | 2.39 | 3.95 | 15.57 | 6.43 | n.e. | 3.89 |
| 8 | 2.11 | n.e. | 1.46 | 1.00 | 2.19 | 1.46 | 1.31 | 2.64 | 10.66 | 5.59 | n.e. | 2.93 |
| 10 | 1.81 | n.e. | 1.07 | 0.69 | 1.37 | 1.06 | 1.13 | 1.70 | 6.68 | 3.14 | n.e. | 1.69 |
| 12 | 1.25 | n.e. | 0.95 | 0.69 | 1.09 | 0.79 | 0.84 | 1.33 | 5.28 | 2.37 | n.e. | 1.32 |
| 16 | 0.70 | n.e. | 0.62 | 0.67 | 0.78 | n.e. | n.e. | 0.78 | 2.56 | 1.13 | n.e. | 0.63 |
| 24 | 0.52 | n.e. | n.e. | n.e. | n.e. | n.e. | n.e. | 0.50 | 1.36 | 0.58 | n.e. | n.e. | n.e. = not evaluable, because lower than the detectable limit of the method.

TABLE 13

PLASMA CONCENTRATION OF RIFAXIMIN (NG/ML) AFTER
ORAL ADMINISTRATION OF TWO 200 MG RIFAXIMIN
TABLETS OF NORMIX ®

| Time (h) | V13 | V14 | V15 | V16 | V17 | V18 | V19 | V20 | V21 | V22 | V23 | V24 |
|---|---|---|---|---|---|---|---|---|---|---|---|---|
| 0 | n.e. | n.e. | n.e. | n.e. | n.e. | n.e. | n.e. | n.e. | n.e. | n.e. | n.e. | n.e. |
| 0.5 | n.e. | 1.00 | 1.50 | 1.47 | n.e. | 3.72 | 2.33 | 14.95 | 1.44 | 5.31 | 2.02 | 1.35 |
| 1 | n.e. | 1.32 | 1.19 | 2.33 | 1.02 | 1.92 | 1.88 | 11.04 | 3.64 | 6.07 | 2.65 | 0.86 |
| 1.5 | 0.50 | 0.84 | 0.82 | 1.97 | 1.26 | 1.54 | 1.35 | 12.13 | 3.12 | 5.15 | 3.03 | 0.58 |
| 2 | 0.52 | 0.78 | 0.84 | 2.39 | 1.09 | 1.03 | 1.17 | 7.27 | 2.63 | 4.42 | 2.75 | 0.50 |
| 3 | 0.76 | 0.54 | 0.54 | 1.11 | 0.63 | 0.71 | 0.74 | 8.47 | 2.40 | 2.78 | 1.58 | n.e. |
| 4 | 0.87 | n.e. | n.e. | 0.64 | n.e. | 0.51 | 0.63 | 3.79 | 1.94 | 2.02 | 1.10 | n.e. |
| 6 | 0.63 | n.e. | n.e. | n.e. | n.e. | n.e. | n.e. | 2.00 | 1.41 | 1.14 | 0.65 | n.e. |
| 8 | n.e. | n.e. | n.e. | n.e. | n.e. | n.e. | n.e. | 1.41 | 0.91 | 0.80 | n.e. | n.e. |
| 10 | n.e. | n.e. | n.e. | n.e. | n.e. | n.e. | n.e. | 0.96 | 0.62 | n.e. | n.e. | n.e. |
| 12 | n.e. | n.e. | n.e. | n.e. | n.e. | n.e. | n.e. | 0.74 | 0.54 | n.e. | n.e. | n.e. |
| 16 | n.e. | n.e. | n.e. | n.e. | n.e. | n.e. | n.e. | n.e. | n.e. | n.e. | n.e. | n.e. |
| 24 | n.e. | n.e. | n.e. | n.e. | n.e. | n.e. | n.e. | n.e. | n.e. | n.e. | n.e. | n.e. | n.e. = not evaluable, because lower than the detectable limit of the method.

The following bioavailability parameters are calculated for comparing the two rifaximin preparations: maximum observed plasma concentration ($C_{max}$); time from administration to obtain $C_{max}$ ($T_{max}$); area under concentration-time curve from time 0 h (first experimental point) up to last sampling (24 h after administration) $AUC_{(0-24\ h)}$. The results are shown in Table 14 and Table 15, in the case of the administration of two 200 mg tablets of rifaximin as described in Example 3 and of two 200 mg tablets of Normix®.

TABLE 14

Arithmetic means of PK parameters of the human subject who received one 200 mg tablet of rifaximin

| | Rifaximin Tablet of Example 3 | | | Normix ® | | |
|---|---|---|---|---|---|---|
| Dose 200 mg | Mean | SD | CV % | Mean | SD | CV % |
| $C_{max}$ (ng/ml) | 3.70 | 1.913 | 51.7 | 1.59 | 1.207 | 75.9 |
| $T_{max}$ (h) | 1.96 | 3.208 | 163.7 | 1.04 | 0.450 | 43.3 |
| $AUC_{0-24\ h}$ (ng/ml × h) | 11.47 | 8.135 | 70.9 | 2.32 | 1.607 | 69.3 |

TABLE 15

Arithmetic means of PK parameters of the human subject who received two 200 mg tablets of rifaximin

| | Preparation of rifaximin of Example 4 | | | Normix ® | | |
|---|---|---|---|---|---|---|
| Dose 400 mg | Mean | SD | CV % | Mean | SD | CV % |
| $C_{max}$ (ng/ml) | 15.01 | 16.225 | 108.1 | 3.54 | 3.883 | 109.7 |
| $T_{max}$ (h) | 1.71 | 1.157 | 67.7 | 1.21 | 1.010 | 83.5 |
| $AUC_{0-24}$ (ng/ml × h) | 63.38 | 63.703 | 100.5 | 10.38 | 13.403 | 129.1 |

Example 5

PK Study on Dogs of Rifaximin Prepared by Spray Drying

Four female beagles received as a single oral administration the rifaximin prepared according to Example 1 at the dosage of 100 mg per kg of body weight of the animal. Capsules of hard gelatin containing only rifaximin were administered, and the pre- and post-dose observations, the body weight and the physical examination were evaluated.

Blood samples were collected from all animals on each day of dosing at: 0 (pre-dose), 1, 2, 4, 6, 8 and 24 hours after each dosing.

The concentration-time curve determines the PK parameters of $AUC_{0-24\ h}$, $C_{max}$ and $T_{max}$ reported in Table 16.

TABLE 16

Mean values of PK parameters of the animals receiving 100 mg/kg of rifaximin

Mean values (±standard error)

| Rifaximin preparation according to Example 1 | $C_{max}$ (ng/ml) | $T_{max}$ (h) | $AUC_{0-24\ h}$ (ng · h/ml) |
|---|---|---|---|
| Dose of 100 mg/kg | 1044.1 ± 588.46 | 2 | 2854.31 ± 1489.87 |

Example 6

Rifaximin Solubility at Different pH

The study was conducted in accordance with accepted principles in order to meet the requirements of the Annex to European Commission Directive 92/69/EEC and the OECD Guidelines for Testing of Chemicals (EEC Method A6, OECD Method 105).

Water solubility was determined in purified water and buffer solutions at pH 4 and 7, by the shake flask method at 20° C.

Aliquots of the saturated solutions of rifaximin-α were adequately diluted, then analyzed by a high performance liquid chromatography (HPLC) method. The solubility of rifaximin was determined versus calibration solutions of rifaximin.

The obtained results are reported in Table 17.

TABLE 17

Rifaximin solubility at different pH

| Solvent system | Solubility (mg/l) |
|---|---|
| Purified water | 3.63 |
| pH 4 buffer solution | 4.12 |
| pH 7 buffer solution | 3.22 |
| pH 10 buffer solution | 299 |

The invention claimed is:

1. A method for producing rifaximin in amorphous form characterized by an X-Ray diffraction spectrum showing diffraction halo peaks in the range 7.75°±0.2-18.33°±0.2, 2θ, with maximum at about 7.75°±0.2 and in the range 14.54°±0.2 and 18.33°±0.2, 2θ, said method comprising:
subjecting a rifaximin solution to a spray-drying treatment in an atomizer by using a nozzle flow with a heated gas at a pressure comprised between 1.0 and 1.5 bar.

2. The method according to claim 1, wherein said rifaximin solution contains an organic solvent.

3. The method according to claim 1, wherein said rifaximin solution comprises an amount of organic solvent comprised between 1 and 40 liters per kg of rifaximin.

4. The method according to claim 1, wherein said gas is air.

5. The method according to claim 1, wherein the produced rifaximin is dried until reaching a constant weight at a temperature between 20° C. and 120° C.

6. The method according to claim 1, wherein the X-Ray diffraction spectrum of the produced rifaximin does not show any peaks characterizing the crystallinity.

7. A method for producing rifaximin in amorphous form characterized by an X-Ray diffraction spectrum showing diffraction halo peaks in the range 7.75°±0.2-18.33°±0.2, 2θ, with maximum at about 7.75°±0.2 and in the range 14.54°±0.2 and 18.33°±0.2, 2θ, said method comprising:
subjecting a rifaximin solution to a spray-drying treatment in an atomizer by using a nozzle flow with a heated gas at a pressure comprised between 0.5 and 2.5 bar.

* * * * *